(12) United States Patent
Simmons et al.

(10) Patent No.: US 10,105,434 B2
(45) Date of Patent: Oct. 23, 2018

(54) IMMUNE ENHANCING RECOMBINANT DENGUE PROTEIN

(71) Applicants: Monika Simmons, Germantown, MD (US); Joseph Robert Putnak, Monongahela, PA (US)

(72) Inventors: Monika Simmons, Germantown, MD (US); Joseph Robert Putnak, Monongahela, PA (US)

(73) Assignees: The United States of America as represented by the Secretary of the Navy, Washington, DC (US); The United States of America as represented by the Sec. of the Army, Washington, DC (US)

( * ) Notice: Subject to any disclaimer, the term of this patent is extended or adjusted under 35 U.S.C. 154(b) by 0 days.

(21) Appl. No.: 15/224,881

(22) Filed: Aug. 1, 2016

(65) Prior Publication Data

US 2017/0035875 A1  Feb. 9, 2017

Related U.S. Application Data

(60) Provisional application No. 62/200,263, filed on Aug. 3, 2015.

(51) Int. Cl.
| | |
|---|---|
| *A61K 39/12* | (2006.01) |
| *C07K 14/005* | (2006.01) |
| *C12N 7/00* | (2006.01) |
| *C12N 9/14* | (2006.01) |
| *A61K 39/00* | (2006.01) |

(52) U.S. Cl.
CPC ............ *A61K 39/12* (2013.01); *C07K 14/005* (2013.01); *C12N 7/00* (2013.01); *C12N 9/14* (2013.01); *C12Y 306/04013* (2013.01); *A61K 2039/5252* (2013.01); *A61K 2039/53* (2013.01); *A61K 2039/545* (2013.01); *A61K 2039/55516* (2013.01); *A61K 2039/57* (2013.01); *A61K 2039/575* (2013.01); *A61K 2039/70* (2013.01); *C07K 2319/21* (2013.01); *C12N 2770/24121* (2013.01); *C12N 2770/24134* (2013.01); *C12N 2770/24171* (2013.01)

(58) Field of Classification Search
None
See application file for complete search history.

(56) References Cited

U.S. PATENT DOCUMENTS

| 5,916,588 A | 6/1999 | Popescu et al. |
| 6,090,406 A | 7/2000 | Popescu et al. |
| 6,254,873 B1 | 7/2001 | Putnak et al. |
| 6,455,509 B1 | 9/2002 | Kochel et al. |
| 7,226,602 B2 | 6/2007 | Whitehead et al. |
| 2013/0071419 A1 | 3/2013 | Ross et al. |

FOREIGN PATENT DOCUMENTS

| WO | WO2014016362 A1 | 1/2014 |
| WO | WO2014204892 A1 | 12/2014 |

OTHER PUBLICATIONS

Liang et al., Cellular and Molecular Immunology, 2016, 13:36-46. (Year: 2016).*
Ben Tinker, CNN Health, Dec. 5, 2017, website http://www.cnn.com/2017/12/04/health/dengue-fever-vaccine-dengvaxia-philippines-intl/index.html, printout 3 pages. (Year: 2017).*
Wan et al., Journal of Biomedical Science, 20:37-45 (2013).
Morefield, G. APPS Journal, 13:191-200 (2011).
Alving, C. et al. Expert Rev. Vaccines 11:733-744 (2012).
Alving, C. et al. Curr Opin Immunol 24:310-315 (2012).
Alving, C. and Rao, M. Vaccine. 26:3036-3045 (2008).
International Search Report for PCT/US16/44976 dated Dec. 8, 2016.
Ranjit S, Kissoon N. Dengue hemorrhagic fever and shock syndromes. Pediatr Crit Care Med. 2011;12(1):90-100. Epub Jul. 20, 2010. doi: 10.1097/PCC.0b013e3181e911a7. PubMed PMID: 20639791.
Halstead SB. Neutralization and antibody-dependent enhancement of dengue viruses. Adv Virus Res. 2003;60:421-67. Epub Dec. 24, 2003. PubMed PMID: 14689700.
Guy B, Barrere B, Malinowski C, Saville M, Teyssou R, Lang J. From research to phase III: preclinical, industrial and clinical development of the Sanofi Pasteur tetravalent dengue vaccine. Vaccine. 2011;29(42):7229-41. Epub Jul. 13, 2011. doi: 10.1016/j.vaccine.2011.06.094. PubMed PMID: 21745521.
Coller BA, Clements DE. Dengue vaccines: progress and challenges. Curr Opin Immunol. 2011;23(3):391-8. Epub Apr. 26, 2011. doi: 10.1016/j.coi.2011.03.005. PubMed PMID: 21514129.
Durbin AP, Whitehead SS. Next-generation dengue vaccines: novel strategies currently under development. Viruses. 2011;3(10):1800-14, Epub Nov. 10, 2011. doi: 10.3390/v3101800. PubMed PMID: 22069516; PubMed Central PMCID: PMC3205382.
Schmitz J, Roehrig J, Barrett A, Hombach J. Next generation dengue vaccines: a review of candidates in preclinical development. Vaccine. 2011;29(42):7276-84. Epub Jul. 26, 2011. doi: 10.1016/j.vaccine.2011.07.017. PubMed PMID: 21781998.
Edelman R. Unique challenges faced by the clinical evaluation of dengue vaccines. Expert Rev Vaccines. 2011;10(2):133-6. Epub Feb. 22, 2011. doi: 10.1586/erv.10.159. PubMed PMID: 21332260.
Thomas SJ. The necessity and quandaries of dengue vaccine development. J Infect Dis. 2011;203(3):299-303. Epub Jan. 7, 2011. doi: 10.1093/infdis/jiq060. PubMed PMID: 21208919; PubMed Central PMCID: PMC3071120.

(Continued)

*Primary Examiner* — Stacy B Chen
(74) *Attorney, Agent, or Firm* — Albert M. Churilla; Diane Tso; Ning Yang

(57) ABSTRACT

The invention relates to a method for preventing, ameliorating or treating disease caused by dengue virus in a subject in need thereof comprising administering to the subject a dengue vaccine formulation in combination with a NS3 helicase polypeptide and/or fragment(s) thereof, wherein said method comprises stimulating humoral as well as cell-mediated immunity to the dengue virus in the subject.

12 Claims, 7 Drawing Sheets

Specification includes a Sequence Listing.

(56) References Cited

OTHER PUBLICATIONS

Endy TP, Anderson KB, Nisalak A, Yoon IK, Green S, Rothman AL, et al. Determinants of inapparent and symptomatic dengue infection in a prospective study of primary school children in Kamphaeng Phet, Thailand. PLoS Negl Trop Dis. 2011;5(3):e975. Epub Mar. 11, 2011. doi: 10.1371/journal.pntd.0000975. PubMed PMID 21390158; PubMed Central PMCID: PMC3046956.
Kaltenbock A, Dubischar-Kastner K, Eder G, Jilg W, Klade C. Kollaritsch H, et al. Safety and immunogenicity of concomitant vaccination with the cell-culture based Japanese Encephalitis vaccine IC51 and the hepatitis A vaccine HAVRIX1440 in healthy subjects. A single-blind, randomized, controlled Phase 3 study. Vaccine. 2009;27(33):4483-9. Epub Jun. 3, 2009. doi: 10.1016/j.vaccine.2009.05.034. PubMed PMID: 19486955.
Putnak R, Barvir DA, Burrous JM, Dubois DR, D'Andrea VM, Hoke CH, et al. Development of a purified, inactivated, dengue-2 virus vaccine prototype in Vero cells: Immunogenicity and protection in mice and rhesus monkeys. J Infect Dis. 1996;174(6):1176-84. Epub Dec. 1, 1996. PubMed PMID: 8940206.
Simmons M, Burgess T, Lynch J, Putnak R. Protection against dengue virus by non-replicating and live attenuated vaccines used together in a prime boost vaccination strategy. Virology. 2010;396(2):280-8. Epub Nov. 17, 2009. doi: 10.1016/j.virol.2009.10.023. PubMed PMID: 19913867.
Fernandez S, Thomas SJ, De La Barrera R, Im-Erbsin R, Jarman RG, Bares B, et al. An adjuvanted, tetravalent dengue virus purified inactivated vaccine candidate induces long-lasting and protective antibody responses against dengue challenge in rhesus macaques. Am J Trop Med Hyg. 2015;92(4):698-708. doi: 10.4269/ajtmh.14-0268. PubMed PMID: 25846281; PubMed Central PMCID: PMC4385761.
Simmons M, Porter KR, Hayes CG, Vaughn DW, Putnak R. Characterization of antibody responses to combinations of a dengue virus type 2 DNA vaccine and two dengue virus type 2 protein vaccines in rhesus macaques. J Virol. 2006;80(19):9577-85. Epub Sep. 16, 2006. doi: 10.1128/JVI.00284-06. PubMed PMID: 16973561; PubMed Central PMCID: PMC1617260.
Stephenson JR. The problem with dengue, Trans R Soc Trop Med Hyg. 2005;99(9):643-6. Epub Jul. 5, 2005. doi: 10.1016/j.trstrnh.2005.05.003. PubMed PMID: 15993908.
Kurane I, Dai LC, Livingston PG, Reed E, Ennis FA. Definition of an HLA-DPw2-restricted epitope on NS3, recognized by a dengue virus serotype-cross-reactive human CD4+ CD8− cytotoxic T-cell clone. J Virol. 1993;67(10):6285-8. Epub Oct. 1, 1993. PubMed PMID: 7690424; PubMed Central PMCID: PMC238054.
Falgout B, Pethel M, Zhang YM, Lai CJ. Both nonstructural proteins NS2B and NS3 are required for the proteolytic processing of dengue virus nonstructural proteins. J Virol. 1991;65(5):2467-75. Epub May 1, 1991. PubMed PMID: 2016768: PubMed Central PMCID: PMC240601.
Falgout B, Miller RH, Lai CJ. Deletion analysis of dengue virus type 4 nonstructural protein NS2B: Identification of a domain required for NS2B-NS3 protease activity. J Virol. 1993:67(4):2034-42. Epub Apr. 1, 1993. PubMed PMID: 8383225; PubMed Central PMCID: PMC240272.
Simmons CP, Dong T, Chau NV, Dung NT, Chau TN, Thao le TT, et al. Early T-cell responses to dengue virus epitopes in Vietnamese adults with secondary dengue virus infections. J Virol. 2005:79(9):5665-75. Epub Apr. 14, 2005. doi: 10.1128/JVI.79.9.5665-5675.2005. PubMed PMID: 15827181; PubMed Central PMCID: PMC1082776.
Haller AA LG, King TH, Kemmler C, Fiolski V, Lu Y, Bellgrau D, Rodell TC, Apelian D, Franzusoff A, Duke RC. Whole recombinant yeast-based immunotherapy induces potent T cell responses targeting HCV NS3 and Core proteins. Vaccine. 2007;25:1452-63.
Jiao X, Wang RY, Qiu Q, Alter HJ, Shih JW. Enhanced hepatitis C virus NS3 specific Th1 immune responses induced by co-delivery of protein antigen and CpG with cationic liposomes. J Gen Virol. 2004;85(Pt 6):1545-53. PubMed PMID: 15166438.

Gao M, Wang H-P, Wang Y-N, Zhou Y, Wang Q-L. HCV-NS3 Th1 minigene vaccine based on invariant chain CLIP genetic substitution enhances CD4+ Th1 cell responses in vivo. Vaccine. 2006;24(26):5491-7.
López L, Venteo A, Jiménez-Clavero MA, Carrasco JL, Cano MJ, Soria E, et al. Evaluation of the baculovirus and E. coli-expressed non-structural (NS) proteins of bluetongue virus (BTV) as antigen in an indirect or competition ELISA to differentiate infected from vaccinated animals. Microbial Cell Factories, 2006;5(Suppl 1):P59.
Wüest T, Both GW, Prince AM, Hofmann C, Löser P. Recombinant ovine atadenovirus induces a strong and sustained T cell response against the hepatitis C virus NS3 antigen in mice. Vaccine. 2004;22(21):2717-21.
Simmons M, Murphy GS, Kochel T, Raviprakash K, Hayes CG. Characterization of antibody responses to combinations of a dengue-2 DNA and dengue-2 recombinant subunit vaccine. Am J Trop Med Hyg. 2001;65(5):420-6. Epub Nov. 22, 2001. PubMed PMID: 11716093.
Russell PK, Nisalak A. Dengue virus identification by the plaque reduction neutralisation test, J Immunol. 1967;99(2):291-6. Epub Aug. 1, 1967. PubMed PMID: 4961907.
Bray M, Zhao BT, Markoff L, Eckels KH, Chanock RM, Lai CJ. Mice immunized with recombinant vaccinia virus expressing dengue 4 virus structural proteins with or without nonstructural protein NS1 are protected against fatal dengue virus encephalitis. J Virol. 1989;63(6):2853-6. Epub Jun. 1, 1989. PubMed PMID: 2724416; PubMed Central PMCID: PMC250798.
Kaufman B, Summers P, Dubois D, Cohen WH, Gentry M. Monoclonal antibodies for dengue virus prM glycoprotein protect mice against lethal dengue infection. Am. J. Trop. Med. Hyg. 1989; 41(5):576-586.
Falgout B, Bray M, Schlesinger JJ, Lai CJ. Immunization of mice wath recombinant vaccinia virus expressing authentic dengue virus nonstructural protein NS1 protects against lethal dengue virus encephalitis. J Virol. 1990;64(9):4356-63. Epub Sep. 1, 1990. PubMed PMID: 2143542; PubMed Central PMCID: PMC247903.
Schlesinger JJ, Brandriss MW, Walsh EE. Protection of mice against dengue 2 virus encephalitis by immunization with the dengue 2 virus non-structural glycoprotein NS1. J Gen Virol. 1987;68 ( Pt 3):853-7. Epub Mar. 1, 1987. PubMed PMID: 3819700.
Zhang YM, Hayes EP, McCarty TC, Dubois DR, Summers PL, Eckels KH, et al. Immunization of mice with dengue structural proteins and nonstructural protein NS1 expressed by baculovirus recombinant induces resistance to dengue virus encephalitis. J Virol. 1988;62(8):3027-31, Epub Aug. 1, 1988. PubMed PMID: 2969058; PubMed Central PMCID: PMC253742.
Mathew A, Rothman AL. Understanding the contribution of cellular immunity to dengue disease pathogenesis, Immunol Rev. 2008;225:300-13. Epub Oct. 8, 2008. doi: 10.1111/j.1600-065X.2008.00678.x. PubMed PMID: 18837790.
Rothman AL. Dengue: defining protective versus pathologic immunity. J Clin Invest. 2004;113(7):946-51. Epub Apr. 2, 2004. doi: 10.1172/JCI21512. PubMed PMID: 15057297; PubMed Central PMCID: PMC379334.
Appanna R, Huat TL, See LL, Tan PL, Vadivelu J, Devi S. Cross-reactive T-cell responses to the nonstructural region of dengue viruses among dengue fever and dengue hemorrhagic fever patients in Malaysia. Clin Vaccine Immunol. 2007;14(8):969-77. Epub Jun. 15, 2007. doi: 10.1126/CVI.00069-07. PubMed PMID: 17567768; PubMed Central PMCID: PMC2044482.
Whitehead SS, Blaney JE, Durbin AP, Murphy BR. Prospects for a dengue virus vaccine. Nat Rev Microbiol. 2007;5(7):518-28. Epub Jun. 15, 2007. doi: 10.1038/nrmicro1690. PubMed PMID; 17558424.
Spaulding AC, Kurane I, Ennis FA, Rothman AL. Analysis of murine CD8(+) T-cell clones specific for the Dengue virus NS3 protein: flavivirus cross-reactivity and influence of infecting serotype. J Virol. 1999;73(1):398-403. Epub Dec. 16, 1998. PubMed PMID: 9847344; PubMed Central PMCID: PMC103845.
Valdés K, Alvarez M, Pupo M, Vázquez S, Rodríguez R, Guzmán MG. Human dengue antibodies against structural and nonstructural proteins. Clin Diagn Lab Immunol. 2000;7(5):856-7.

(56) References Cited

OTHER PUBLICATIONS

Churdboonchart V, Bhamarapravati N, Peampramprecha S, Sirinavin S. Antibodies against dengue viral proteins in primary and secondary dengue hemorrhagic fever. Am J Trop Med Hyg. 1991;44(5):481-93. Epub May 1, 1991. PubMed PMID: 2063952.

Konishi E, Ajiro N, Nukuzuma C, Mason PW, Kurane I. Comparison of protective efficacies of plasmid DNAs encoding Japanese encephalitis virus proteins that induce neutralizing antibody or cytotoxic T lymphocytes in mice. Vaccine. 2003;21(25):3675-83.

Morozova OV, Maksimova TG, Bakhvalova VN. Tick-borne encephalitis virus NS3 gene expression does not protect mice from homologous viral challenge. Viral Immunol. 1999;12(4):277-80.

Rau H, Revets H, Balmelli C, McCullough KC, Summerfield A. Immunological properties of recombinant classical swine fever virus NS3 protein in vitro and in vivo. Vet Res. 2006;37(1):155-68.

Álvarez-Rodriguez LM, Ramos-Ligonio A, Rosales-Encina JL, Martinez-Cázares MT, Parissi-Crivelli A, López-Monteon A. Expression, purification, and evaluation of diagnostic potential and immunogenicity of a recombinant NS3 protein from all serotypes of dengue virus. J Trop Med. 2012;2012.

Ramirez R, Falcón, R, Izquierdo A, Garcia A, Alvarez M, Perez AB, et al. Recombinant dengue 2 virus NS3 protein conserves structural antigenic and immunological properties relevant for dengue vaccine design. Virus Genes. 2014;49(2):185-95.

Costa SM, Yorlo AP, Gonsalves A, Vidale MM, Costa E, Mohana-Borges R, et al. Induction of a protective response in mice by the dengue virus NS3 protein using DNA vaccines. PLoS One. 2011;6(10):e25685.

Vogelzang A, Perdomo C, Zedler U, Kuhlmann S, Hurwitz R, Gengenbacher M, et al. Central memory CD4+ T cells are responsible for the recombinant Bacillus Calmette-Guerin DeltaureC::hly vaccine's superior protection against tuberculosis, J Infect Dis. 2014;210(12):1928-37. doi: 10.1093/infdis/jiu347. PubMed PMID: 24943726: PubMed Central PMCID: PMCPMC4241943.

Sitati EM, Diamond MS. CD4+ T-cell responses are required for clearance of West Nile virus from the central nervous system. J Virol. 2006;80(24):12060-9.

Brien JD, Uhrlaub JL, Nikolich-Žugich J. West Nile virus-specific CD4 T cells exhibit direct antiviral cytokine secretion and cytotoxicity and are sufficient for antiviral protection. The Journal of Immunology, 2008:181(12):8568-75.

Rivino L, Kumaran EA, Jovanovic V, Nadua K, Teo EW, Pang SW, et al. Differential Targeting of Viral Components by CD4+ versus CD8+ T Lymphocytes in Dengue Virus Infection. J Virol. 2013; 87(5):2693-2706.

Beckett CG, et al. Vaccine, 29:960-968 (2011).

Coller BA et al., Vaccine, 29:7267-75 (2011).

\* cited by examiner

```
5041  GACAACCCAG  AGATCGAAGA  TGACATTTTC  CGAAAGAGAA  GACTGTGACCAT  CATGGACCTC
5101  CATCCAGGAG  CGGGAAGAC   GAAAAGATAC  CTTCCGGCCA  TAGTCAGAGA    AGCTATAAAA
5161  CGGGGTTTGA  GAACATTAAT  CTTGGCTCCC  ACTAGAGTTG  TGGCAGCTGA    AATGGAGGAA
5221  GCTCTTAGAG  GACTTCCAAT  AAGATACCAA  ACCCCAGCCA  TCAGAGCTGA    GCACATCGGG
5281  CGGGAGATTG  TGGACCTAAT  GTGTCATGCC  ACATTTACCA  TCAGGCTGCT    ATCACCAGTT
5341  AGAGTGCCAA  ACTACAACCT  GATTATCATG  GACGAAGCCC  ATTCACAGA     CCCAGCAAGT
5401  ATAGCAGCCA  GAGGATACAT  CTCAACTCGA  GTGGAGATGG  GTGACGCAGC    TGGGATTTTC
5461  ATGACAGCCA  CTCCCCGGG   AAGCAGAGAC  CCATTTCCTC  AGAGCAATGC    ACCAATCATA
5521  GATGAAGAAA  GAGAAATCCC  TGAACGTTCG  TGGAATTCTG  GACATGAGTG    GGTCACGGAT
5581  TTCAAAGGGA  AGATCGTTG   GTTCGTTCCA  AGTATAAAAG  CAGGAAATGA    TATAGCAGCT
5641  TGCCTGAGAA  AAAATGCAAA  GAAAGTGATA  CAACTCAGTA  GGAACACTTT    TGATTCTGAG
5701  TATGTCAAGA  CTAGAACCAA  TGATTGGGAT  TTCGTGGTTA  CAACTGACAT    TTCAGAAATG
5761  GGTGCCAATT  TCAAGGCTGA  GAGGGTTATA  GACCCCAGAC  GCTGCATGAA    ACCAGTCATA
5821  CTAACAGATG  GTGAGGAGCG  GGTGATTCTG  GCAGGACCTA  TGCCAGTGAC    CCAACTCTAGT
5881  GCAGCACACA  GAAGAGGGAG  AATAGGAAGA  AATGATGAA   ACTGGAAAGA    CCAGTACATA
5941  TACATGGGGG  AACCCTGGA   ACATCAACAC  ACCAGAAGGA  GACTGTGCAC    AGCCAAAATG
6001  CTCCTAGATA  ACATCAACAC  ACCAGAAGGA  ATCATCCCTA  GCATGTTCGA    ACCAGAGCGT
6061  GAAAAGTGG   ATGCCATTGA  TGGCGAATAC  CGCTTGAGAG  GAGAAGCAAG    GAAAACCTTT
6121  GTAGACTTAA  TGAGAAGAGG  AGACCTACCA  GTCTGGTTGG  CCTACAAAGT    GGCAGCTGAA
6181  GGCATCAACT  ACGCAGAC (SEQ ID NO. 5)
```

FIGURE 6

DNPEIEDDIFRKRRLTIMDLHPGAGKTKRYLPAIVREAIKRGLRTLILAPTRVVAAEMEE
ALRGLPIRYQTPAIRAEHTGREIVDLMCHATFTMRLLSPVRVPNYNLIIMDEAHFTDPAS
IAARGYISTRVEMGEAAGIFMTATPPGSRDPFPQSNAPIIDEEREIPERSWNSGHEWVTD
FKGKTVWFVPSIKAGNDIAACLRKNGKKVIQLSRKTFDSEYVKTRTNDWDFVVTDIS
EMGANFKAERVIDPRRCMKPVILTDGEERVILAGPMPVTHSSAAQRRGRIGRNPKNEN
DQYIYMGEPLENDEDCAHWKEAKMLLDNINTPEGIIPSMFEPEREKVDAIDGEYRLRG
EARKTFVDLMRRGDLPVWLAYKVAAEGINYAD                (SEQ ID NO.6)

FIGURE 7

SEQUENCE LISTING

<160> NUMBER OF SEQ ID NOS: 6

<210> SEQ ID NO 1
<211> LENGTH: 30
<212> TYPE: DNA
<213> ORGANISM: Dengue virus

<400> SEQUENCE: 1
catatggaag aacaaacact gaccatactc                                    30

<210> SEQ ID NO 2
<211> LENGTH: 31
<212> TYPE: DNA
<213> ORGANISM: Dengue virus

<400> SEQUENCE: 2
gcggccgcat ggaggtccat gatggtcagt c                                  31

<210> SEQ ID NO 3
<211> LENGTH: 30
<212> TYPE: DNA
<213> ORGANISM: Dengue virus

<400> SEQUENCE: 3
catatggaca acccagagat cgaagatgac                                    30

<210> SEQ ID NO 4
<211> LENGTH: 32
<212> TYPE: DNA
<213> ORGANISM: Dengue virus

<400> SEQUENCE: 4
gcggccgcgt ctgcgtagtt gatgccttca gc                                 32

<210> SEQ ID NO 5
<211> LENGTH: 1158
<212> TYPE: DNA
<213> ORGANISM: Dengue virus

<400> SEQUENCE: 5
gacaacccag agatcgaaga tgacattttc cgaaagagaa gactgaccat catggacctc    60
catccaggag cgggaaagac gaaaagatac cttccggcca tagtcagaga agctataaaa   120
cggggtttga acattaat cttggctccc actagagttg tggcagctga atggaggaa     180 gctcttagag gacttccaat aagataccaa accccagcca tcagagctga gcacaccggg   240
cgggagattg tggacctaat gtgtcatgcc acatttacca tgaggctgct atcaccagtt   300
agagtgccaa actacaacct gattatcatg gacgaagccc atttcacaga cccagcaagt   360
atagcagcca gaggatacat ctcaactcga gtggagatgg gtgaggcagc tgggattttc   420
atgacagcca ctcccccggg aagcagagac ccatttcctc agagcaatgc accaatcata   480
gatgaagaaa gagaaatccc tgaacgttcg tggaattctg acatgagtg ggtcacggat    540 ttcaaaggga agactgtttg gttcgttcca agtataaaag caggaaatga tatagcagct   600
tgcctgagaa aaatggaaa gaaagtgata caactcagta ggaagacttt tgattctgag    660
tatgtcaaga ctagaaccaa tgattgggat ttcgtggtta caactgacat ttcagaaatg   720
ggtgccaatt tcaaggctga gagggttata gaccccagac gctgcatgaa accagtcata   780
ctaacagatg gtgaggagcg ggtgattctg gcaggaccta tgccagtgac ccactctagt   840
gcagcacaaa gaagagggag aataggaaga aatccaaaaa atgaaaatga ccagtacata   900

```
tacatgggggg  aacctctgga  aaatgatgaa  gactgtgcac  actggaaaga  agccaaaatg    960
ctcctagata  acatcaacac  accgaaagga  atcatccta  gcatgttcga  accagagcgt   1020
gaaaaagtgg  atgccattga  tggcgaatac  cgcttgagag  gagaagcaag  gaaaaccttt   1080
gtagacttaa  tgagaagagg  agacctacca  gtctggttgg  cctacaaagt  ggcagctgaa   1140
ggcatcaact  acgcagac                                                     1158
```

<210> SEQ ID NO 6
<211> LENGTH: 386
<212> TYPE: PRT
<213> ORGANISM: Dengue virus

<400> SEQUENCE: 6

```
Asp Asn Pro Glu Ile Glu Asp Asp Ile Phe Arg Lys Arg Arg Leu Thr
1               5                   10                  15

Ile Met Asp Leu His Pro Gly Ala Gly Lys Thr Lys Arg Tyr Leu Pro
            20                  25                  30

Ala Ile Val Arg Glu Ala Ile Lys Arg Gly Leu Arg Thr Leu Ile Leu
        35                  40                  45

Ala Pro Thr Arg Val Val Ala Ala Glu Met Glu Glu Ala Leu Arg Gly
    50                  55                  60

Leu Pro Ile Arg Tyr Gln Thr Pro Ala Ile Arg Ala Glu His Thr Gly
65                  70                  75                  80

Arg Glu Ile Val Asp Leu Met Cys His Ala Thr Phe Thr Met Arg Leu
                85                  90                  95

Leu Ser Pro Val Arg Val Pro Asn Tyr Asn Leu Ile Ile Met Asp Glu
            100                 105                 110

Ala His Phe Thr Asp Pro Ala Ser Ile Ala Ala Arg Gly Tyr Ile Ser
        115                 120                 125

Thr Arg Val Glu Met Gly Glu Ala Ala Gly Ile Phe Met Thr Ala Thr
    130                 135                 140

Pro Pro Gly Ser Arg Asp Pro Phe Pro Gln Ser Asn Ala Pro Ile Ile
145                 150                 155                 160

Asp Glu Glu Arg Glu Ile Pro Glu Arg Ser Trp Asn Ser Gly His Glu
                165                 170                 175

Trp Val Thr Asp Phe Lys Gly Lys Thr Val Trp Phe Val Pro Ser Ile
            180                 185                 190

Lys Ala Gly Asn Asp Ile Ala Ala Cys Leu Arg Lys Asn Gly Lys Lys
        195                 200                 205

Val Ile Gln Leu Ser Arg Lys Thr Phe Asp Ser Glu Tyr Val Lys Thr
    210                 215                 220

Arg Thr Asn Asp Trp Asp Phe Val Val Thr Thr Asp Ile Ser Glu Met
225                 230                 235                 240

Gly Ala Asn Phe Lys Ala Glu Arg Val Ile Asp Pro Arg Arg Cys Met
                245                 250                 255

Lys Pro Val Ile Leu Thr Asp Gly Glu Glu Arg Val Ile Leu Ala Gly
            260                 265                 270

Pro Met Pro Val Thr His Ser Ser Ala Ala Gln Arg Arg Gly Arg Ile
        275                 280                 285

Gly Arg Asn Pro Lys Asn Glu Asn Asp Gln Tyr Ile Tyr Met Gly Glu
    290                 295                 300

Pro Leu Glu Asn Asp Glu Asp Cys Ala His Trp Lys Glu Ala Lys Met
305                 310                 315                 320
```

-continued

```
Leu Leu Asp Asn Ile Asn Thr Pro Glu Gly Ile Ile Pro Ser Met Phe
            325             330             335

Glu Pro Glu Arg Glu Lys Val Asp Ala Ile Asp Gly Glu Tyr Arg Leu
            340             345             350

Arg Gly Glu Ala Arg Lys Thr Phe Val Asp Leu Met Arg Arg Gly Asp
        355             360             365

Leu Pro Val Trp Leu Ala Tyr Lys Val Ala Ala Glu Gly Ile Asn Tyr
    370             375             380

Ala Asp
385
```

IMMUNE ENHANCING RECOMBINANT DENGUE PROTEIN

CROSS REFERENCE TO RELATED APPLICATIONS

The present application claims the benefit of U.S. Provisional Patent Application No. 62/200,263 filed Aug. 3, 2015, the entire disclosure of which is incorporated by reference herein.

SEQUENCE LISTING

The instant application contains a Sequence Listing which has been submitted in ASCII format via EFS-Web and is hereby incorporated by reference in its entirety. Said ASCII copy, created on Jul. 28, 2016 is named "NC103701_ST25.txt" and is 5.81 kilobytes in size.

BACKGROUND OF INVENTION

Field of the Invention

The inventive subject matter comprises an immune enhancing composition comprising a recombinant protein derived from the dengue virus non-structural NS3 helicase. The recombinant protein is useful in vaccine formulations to provide enhanced immunity against antigens including dengue virus antigens.

Description of Related Art

Dengue is a rapidly emerging mosquito-borne (*Aedes aegypti*) viral infection of humans, with an estimated 2.5 billion people at risk worldwide. It has been estimated that the dengue viruses (DENVs) cause 50-100 million clinically apparent infections and up to 50,000 deaths each year. DENVs are members of the family Flaviviridae and are comprised of four antigenically related serotypes (serotypes 1-4). Most clinical infections result in a self-limited, acute febrile illness called dengue fever (DF), however, several hundred thousand cases of severe life-threatening dengue hemorrhagic fever (DHF) and dengue shock syndrome (DSS) also occur annually. The risk of DHF and DSS appears to be increased by the presence of antibodies from a previous dengue infection. This is hypothesized to be due to antibody-dependent enhancement (ADE) of infection by preexisting "enhancing" antibodies which form immune complexes capable of increasing viral infection in Fc receptor-bearing monocytic cells and macrophages. Due to the risk associated with secondary infections, ideally, a successful vaccine candidate would have to confer equal and effective protection against all four serotypes simultaneously.

A successful DENV vaccine currently remains an elusive goal. Several groups are currently evaluating live attenuated DENV vaccine candidates in clinical trials (Guy, et al., Vaccine, 29: 7229-41 (2011); Coller, B. A., D. E. Clements, Current Opinion in Immunology, 23: 391-8 (2011); Durbin, A. P., S. S. Whitehead, Viruses, 3: 1800-14 (2011); Schmitz, et al., Vaccine, 29: 7276-84 (2011); Edelman, R., Expert Review of Vaccines, 10: 133-6 (2011)); Thomas, S. J., Journal of Infectious Diseases, 203: 299-303 (2011); Endy, et al. PloS Neglected Tropical Diseases, 5:e975 (2011)). Major obstacles for the development of live virus vaccines include low seroconversion rates, prolonged immunization schedules, and sometimes, vaccine reactogenicity. As an alternative, non-replicating vaccines have been developed that could potentially shorten the dosing schedule and provide a safer preparation that can be administered to children, chronically ill or immunosuppressed individuals. The recently licensed Vero cell-derived purified inactivated vaccine (PIV) for Japanese encephalitis, for example, induced high-titer and long-lasting neutralizing antibody responses within two months (Kaltenbock, et al., Vaccine, 27: 4483-9 (2009)).

A purified inactivated DENV-2 PIV candidate has been developed which contains DENV C, prM, and E antigens, along with smaller amounts of NS1 antigen (Putnak, et al., J. Inf. Dis., 174: 1176-84 (1996)). This vaccine was tested in rhesus macaques where it was demonstrated to elicit virus neutralizing antibodies and protect against wild-type virus challenge three months after vaccination. A virus neutralizing antibody titer of 1:80 was estimated to be the minimum titer required for protection. In a subsequent study in rhesus macaques, a tetravalent DENV (TDENV) PIV administered on a 0, 30-day schedule, resulted in neutralizing antibody responses against all four DENV serotypes 1 month after the second dose (Simmons, et al., Virology, 396: 280-8 (2010)).

A recent report describes the protective antibody responses of a TDENV PIV against all four DENV serotypes in rhesus macaques (Fernandez, et al., Amer. J. Trop. Med. Hyg., 92: 698-708 (2015)). In this study, animals received 2 μg (0.5 μg per serotype) of TDENV adjuvanted with 0.1% alum on days 0 and 28. All animals had a peak neutralizing antibody titer one month after the second dose against each of the four DENV serotypes. Groups of animals were challenged with live DENV-2 or DENV-1 on days 252 (32 weeks post-dose 2) and 308 (40 weeks post-dose 2), respectively. There was no measurable viremia after DENV-2 challenge and only 0.2 mean days of viremia in the group that was challenged with DENV-1. However, most animals had detectable RNA in their serum (RNAemia) over several days after challenge, indicating sterile immunity was not achieved. The authors commented that vaccine-induced cell mediated immunity (CMI) may play a critical role in reducing viral load after infection. While these results suggest that the DENV PIV vaccine may elicit high-titered virus neutralizing antibodies, it might not be as effective at eliciting cell-mediated immune responses and conferring long-term protection (Simmons, et al., J. Virology, 80: 9577-85 (2006)). Thus, there remains the continued need for more efficacious dengue vaccines, including dengue PIV vaccines which provide longer term protection against DENVs. Specifically, there is a continuing need to develop a more effective purified inactivated dengue virus vaccine that can stimulate humoral as well as cell-mediated immunity.

SUMMARY OF THE INVENTION

Thus, in a first aspect, the present invention relates to a method of preventing, ameliorating or treating disease caused by dengue virus in a subject in need thereof comprising administering to the subject a dengue vaccine formulation in combination with a NS3 helicase polypeptide and/or fragment(s) thereof, wherein said method comprises stimulating humoral as well as cell-mediated immunity to the dengue virus in the subject. In one embodiment, the dengue vaccine formulation and the NS3 helicase polypeptide and/or fragments thereof are administered separately. In another embodiment, the NS3 helicase polypeptide and/or fragments thereof are administered to the subject as nucleic acid encoding the NS3 helicase polypeptide and/or fragment(s) thereof. In a particular embodiment, the nucleic acid may be administered as a DNA vaccine.

In another embodiment, the dengue vaccine formulation and the NS3 helicase polypeptide and/or fragments thereof are administered together. In particular embodiments, the dengue vaccine formulation is administered to the subject in the form of a composition comprising the NS3 helicase and/or fragments thereof as an additional active pharmaceutical ingredient, e.g., as a pharmaceutical composition, more particularly, as a dengue vaccine formulation, comprising the NS3 helicase protein and/or fragments thereof. In another embodiment, the dengue vaccine formulation may comprise nucleic acid encoding the NS3 helicase polypeptide and/or fragments thereof, wherein the NS3 helicase polypeptide and/or fragments thereof are administered to the subject as nucleic acid encoding the NS3 helicase polypeptide and/or fragment(s) thereof. In a particular embodiment, the nucleic acid is administered to the subject as a DNA vaccine.

In another aspect, the instant invention relates to methods of enhancing an immune response against one or more flaviviruses in a subject comprising administering a flavivirus vaccine in combination with the helicase domain of NS3 polypeptide and/or fragments thereof. In a particular embodiment, the flavivirus vaccine is a dengue virus vaccine.

In another aspect, the invention relates to compositions comprising a viral vaccine formulation in combination with a NS3 helicase polypeptide and/or fragments thereof, and/or nucleic acid encoding the NS3 helicase protein and/or fragments thereof. In a particular embodiment, the viral vaccine formulation is a dengue vaccine formulation. In a particular embodiment, the composition is a pharmaceutical composition. In a particular embodiment, the composition is, and/or may comprise, a DNA vaccine.

In another aspect, the invention relates to immunogenic compositions comprising a NS3 helicase polypeptide and/or one or more fragments thereof, and/or nucleic acid encoding said NS3 helicase polypeptide and/or fragments thereof, and an effective amount of one or more adjuvants. In a particular embodiment the composition is a pharmaceutical composition. In a particular embodiment, the composition is a DNA vaccine. In another embodiment, the NS3 helicase polypeptide comprises amino acids 174-560 of the NS3 helicase. In another embodiment, the NS3 helicase polypeptide comprises amino acids 200-324 of the NS3 helicase. In another embodiment, the NS3 helicase polypeptide comprises T cell epitopes. In another embodiment, the composition further comprises a flavivirus vaccine formulation. In a particular embodiment, the flavivirus vaccine formulation is a dengue vaccine formulation. In another embodiment, the dengue vaccine formulation is a dengue purified inactivated vaccine. In yet another embodiment, the dengue purified inactivated vaccine is a dengue virus-2 purified inactivated vaccine. In yet another embodiment, the dengue vaccine formulation is a dengue vaccine lacking its own functional NS3 helicase gene/protein. In particular embodiments, the dengue vaccine is in the form of a chimeric or genetically modified live attenuated vaccine, recombinant subunit vaccine, or a DNA vaccine.

In yet another aspect, the invention relates to pharmaceutical compositions comprising a nucleic acid sequence encoding a NS3 helicase polypeptide and/or fragments thereof. In a particular embodiment, the nucleic acid encodes T cell epitopes. In a particular embodiment, the nucleic acid comprises a sequence which encodes amino acids 174-560 of the NS3 helicase. In another embodiment, the nucleic acid comprises a sequence which encodes amino acids 200-324 of the NS3 helicase. In a particular embodiment, the nucleic acid is a DNA plasmid comprising a nucleic acid sequence which encodes NS3 helicase and/or fragments thereof. In a particular embodiment, the pharmaceutical composition is a DNA vaccine.

In particular embodiments of the various above aspects, the vaccine formulation is directed against a flavivirus. In a particular embodiment, the vaccine is a dengue vaccine formulation directed against one or more dengue viruses of serotypes 1-4. In a particular embodiment, the dengue vaccine formulation comprises one or more antigens selected from the group consisting of a Dengue-1 virus antigen, a Dengue-2 virus antigen, a Dengue-3 virus antigen and a Dengue-4 virus antigen. In a particular embodiment, the dengue vaccine formulation is a DNA vaccine. In another embodiment, the dengue vaccine formulation is a dengue purified inactived vaccine. In a particular embodiment, the dengue vaccine formulation is a tetravalent dengue purified inactived vaccine. In another embodiment, the dengue vaccine formulation is a dengue virus-2 purified inactivated vaccine.

In particular embodiments of the various above aspects, the NS3 helicase is a recombinant protein. In another embodiment, the NS3 helicase polypeptide or fragments comprise one or more T-cell epitopes. In a particular embodiment, the polypeptide or fragments comprise amino acids 174-560 of the NS3 helicase. In another embodiment, the polypeptide or fragments comprise amino acids 200-324 of the NS3 helicase. In a particular embodiment, the polypeptide or fragments consists of, or consists essentially of, amino acids 174-560 of the NS3 helicase. In another embodiment, the polypeptide or fragments consists of, or consists essentially of, amino acids 200-324 of the NS3 helicase.

BRIEF DESCRIPTION OF THE DRAWINGS

FIG. 1 depicts a schematic diagram of the DENV-2 genome (A) and the regions coded by the different recombinant plasmids (B). Dengue virus is a single-stranded, positive-sense RNA genome of about 11 kb in length. The open reading frame encodes the structural proteins capsid (C), membrane (M), envelope (E) and seven nonstructural proteins (NS1, NS2A, NS2B, NS3, NS4A, NS4B and NS5). The region linking the protease domain and helicase domain of NS3 (residues 169 to 179) are shown in the stippled region. The last 40 residues of NS2b (90 to 130) were added to the NS3 protease (NS3Pro) fragment (1 to 196). The NS3 helicase (NS3Hel) fragment contains residues 174 to 560.

FIG. 2 depicts serum IgG anti-DENV-2 antibody responses in immunized mice measured by ELISA using purified virions. Bars indicate reciprocal geometric mean endpoint titers (GMT)≥0.1 $OD_{405}$. For calculation purposes titers<100 were assigned a value of 5. PIV=purified inactivated vaccine, Pro=protease, Hel=helicase.

FIG. 3 depicts anti-DENV-2 neutralizing antibody responses in immunized mice on Day 35 after first inoculation. Neutralizing antibody titers were determined for each animal by plaque reduction neutralization test (PRNT). The Y-axis indicates reciprocal 50% PRNT ($PRNT_{50}$) titers ($Log_{10}$). For calculation purposes, titers<20 were given a value of 5. PIV=purified inactivated vaccine, Pro=protease, Hel=helicase.

FIG. 4 depicts T-cell responses induced by vaccination with recombinant protein. Groups of vaccinated mice were tested for IFN-γ responses using a standard ELISPOT assay.

Mouse spleen cells collected on Day 35 after first immunization were stimulated with overlapping peptide pools spanning the entire M, E and NS3 protein. Responses are presented as number of spots per one million cells. Results indicate the mean of 3 mice with error bars equal to one standard deviation. PIV=purified inactivated vaccine, Pro=protease, Hel=helicase, E=envelope, M=membrane.

FIG. 5 depicts depletion of CD4+ and CD8+ T cell subsets followed by IFN-γ ELISPOT. Whole spleen cells (a) or spleen cells depleted with either CD8+ or CD4+ subset (b, c), were stained with anti-mouse CD4+ or CD8+ monoclonal antibodies. The % of each subset is shown. IFN-γ response from whole or subset-depleted spleen cells was measured by ELISPOT assay (d). Results represent number of spots per million cells. Control=media without peptides.

FIG. 6 depicts the dengue virus NS3 recombinant helicase DNA sequence encoding amino acids 174-560 (NTs 5041-6198 in strain S16803) (SEQ ID NO. 5).

FIG. 7 depicts the 386 amino acid sequence of the dengue virus NS3 recombinant helicase construct (amino acid residues 174-560) (SEQ ID NO. 6).

DETAILED DESCRIPTION OF PREFERRED EMBODIMENTS

Figure 1:
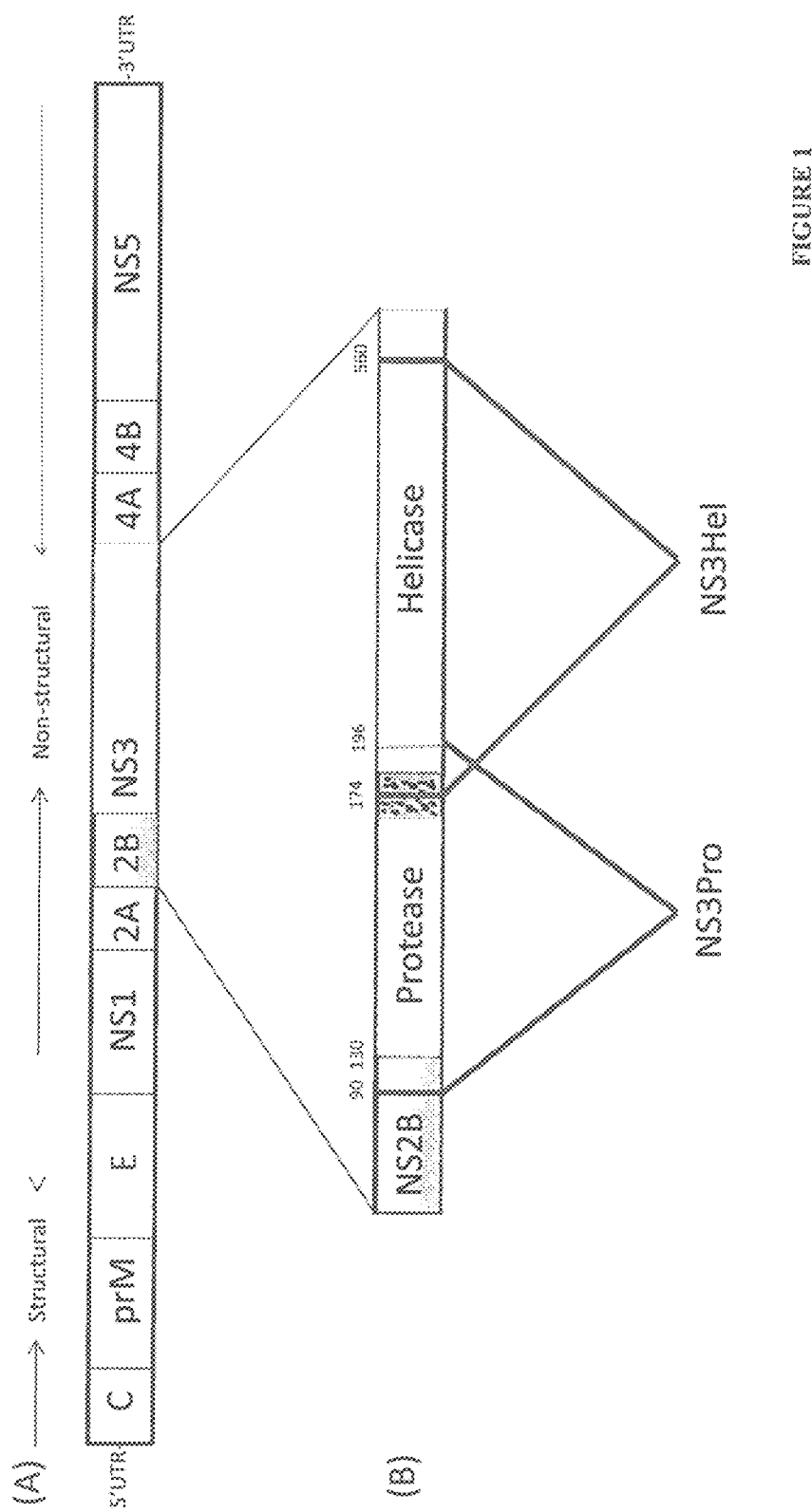

While the specification concludes with the claims particularly pointing out and distinctly claiming the invention, it is believed that the present invention will be better understood from the following description.

All percentages and ratios used herein are by weight of the total composition unless otherwise indicated herein. All temperatures are in degrees Celsius unless specified otherwise. All measurements made are at 25° C. and normal pressure unless otherwise designated. The present invention can "comprise" (open ended) or "consist essentially of" the components of the present invention as well as other ingredients or elements described herein. As used herein, "comprising" means the elements recited, or their equivalent in structure or function, plus any other element or elements which are not recited. The terms "having" and "including" are also to be construed as open ended unless the context suggests otherwise. As used herein, "consisting essentially of" means that the invention may include ingredients in addition to those recited in the claim, but only if the additional ingredients do not materially alter the basic and novel characteristics of the claimed invention.

All ranges recited herein include the endpoints, including those that recite a range "between" two values. Terms such as "about," "generally," "substantially," "approximately" and the like are to be construed as modifying a term or value such that it is not an absolute, but does not read on the prior art. Such terms will be defined by the circumstances and the terms that they modify as those terms are understood by those of skill in the art. This includes, at very least, the degree of expected experimental error, technique error and instrument error for a given technique used to measure a value. Unless otherwise indicated, as used herein, "a" and "an" include the plural, such that, e.g., "an antigen" can mean at least one antigen, as well as a plurality of antigens, i.e., more than one antigen.

Where used herein, the term "and/or" when used in a list of two or more items means that any one of the listed characteristics can be present, or any combination of two or more of the listed characteristics can be present. For example, if a composition of the instant invention is described as containing characteristics A, B, and/or C, the composition can contain A feature alone; B alone; C alone; A and B in combination; A and C in combination; B and C in combination; or A, B, and C in combination. The entire teachings of any patents, patent applications or other publications referred to herein are incorporated by reference herein as if fully set forth herein.

The two effector arms of the immune system relevant to protection from viral disease in humans are neutralizing antibodies and cytotoxic T lymphocytes. As part of the adaptive immune response, naïve T cells encounter specific antigen in the context of MHC class I (CD8+ T-cell epitopes) or MHC class II (CD4+ T-cell epitopes) molecules on the surface of antigen presenting cells (APCs). T cells proliferate and differentiate into a mixture of short-lived effector cells and long-lived memory cells. The CD4+ effector cells fall into two functional classes of helper T cells ($T_H$): $T_H 1$ cells, whose function is to activate macrophages to eliminate intracellular pathogen; and $T_H 2$ cells, which activate B cells to make antibody and to promote the development of memory cells. CD4+ T cells are also crucial for the generation of functional and protective antigen-specific CD8+ T cells which have the unique capability of killing infected cells and are therefore important for viral clearance. The goal of an effective vaccine is to generate specific memory cells that can prevent future infections and disease.

As discussed briefly above, cell-mediated immune responses may be important in conferring long-term protection in a subject (Simmons, et al., J. of Virology, 80: 9577-85 (2006)). How T cells contribute to the immune response in dengue disease has not been clearly defined. It has been hypothesized that the dengue virus nonstructural protein 3 (NS3) protein may be useful as an additional vaccine component due to its stimulation of cell-mediated immunity (Stephenson, J. R., Transactions of the Royal Society of Tropical Medicine and Hygiene, 99: 643-6 (2005)). Indeed, NS3 is considered the main target for CD4+ and CD8+ T cell responses during dengue infection and may be involved in protection (Mathew A, Rothman A L., Immunol Rev. 225: 300-13 (2008); Rothman A L. J Clin Invest. 113:946-51 (2004); Appanna R, et al., Clin Vaccine Immunol., 14:969-77 (2007). In a comprehensive analysis of the T cell response in Vietnamese adults, more than half recognized DENV-2 NS3 CD4+ and CD8+ epitopes (Simmons C P, et al. J Virol. 79:5665-75 (2005)). This study identified 30 T-cell epitopes on the NS3 protein with 24 (80%) within the helicase domain. Because T cells do not recognize intact virions, dengue virus-specific T cells would not be able to provide sterilizing immunity against viral infection.

In addition to a variety of T cell responses, immune responses induced by dengue virus infection can include antibody responses to various structural and nonstructural proteins. For example, antibodies to non-structural protein NS1 have been reported to protect mice against challenge with dengue virus (Falgout B, et al., J Virol., 64:4356-63 (1990); Schlesinger J J, et al., J Gen Virol., 68:853-7 (1987); Zhang Y M, et al. J Virol. 62:3027-31 (1988)). Purified inactivated vaccines contain structural proteins C, prM, E and non-structural protein NS1, with the E protein containing most of the epitopes that elicit neutralizing antibodies (Whitehead S S, et al., Nat Rev Microbiol. 5:518-28 (2007)). DNA vaccines containing nucleotides coding for prM and E proteins are disclosed in Beckett C G, et al., Vaccine, 29:960-968 (2011). Recombinant subunit vaccines containing prM and truncated E proteins are disclosed in Coller B A et al., Vaccine, 29:7267-75 (2011). Antibodies against structural proteins prM and E have been shown to neutralize flaviviruses (Bray M, et al. J Virol. 1989 63:2853-6 (1989); Kaufman B, et al., DTIC Document, 1989)).

Anti-NS3 antibodies have been detected in human sera of patients with primary and secondary DENV infections (Valdés K, et al., Clin Diagn Lab Immunol., 7:856-7 (2000); Churdboonchart V. et al., Am J Trop Med Hyg. 44:481-93 (1991)). Notably, although purified recombinant NS3 proteins were able to induce strong anti-NS3 antibody responses in mice, they were not neutralizing antibodies (Valdés K, et al., Clin Diagn Lab Immunol., 7:856-7 (2000); Álvarez-Rodriguez L M, et al., J Trop Med. 2012; 2012; Ramirez R, et al., Virus Genes, 49:185-95 (2014)). Studies employing a DNA vaccine based on NS3 from Japanese encephalitis virus provided only partial protection against live virus challenge (Konishi E, et al. Vaccine, 21:3675-83 (2003)). Other studies using a DNA based vaccine encoding NS3 from tick-borne encephalitis virus revealed absence of protection in mice, whereas a vaccine encoding NS3 in addition to E2 glycoprotein indicated an increased neutralizing antibody response and IFN-γ responses induced by CD4+ T helper cell and CD8+ cytotoxic T cells (Morozova O V, et al. Viral Immunol. 12:277-80(1999); Rau H, et al., Vet Res. 37:155-68 (2006)).

We investigated the possibility of developing a more effective purified inactivated dengue virus vaccine that would reliably stimulate humoral as well as cell-mediated immunity in a subject. Specifically, we evaluated the incorporation of recombinant subunit NS3 proteins representing protease and/or helicase as components of a DENV-2 PIV vaccine to determine if they generate better T-cell responses than the DENV PIV vaccine alone. As described in detail in the below examples, our studies unexpectedly revealed that in addition to stimulation of cell-mediated immunity, NS3 protein is also a potent modulator of humoral immune responses to dengue antigen. In particular, it was discovered that the helicase region of the NS3 protein could significantly enhance not only the cell mediated immune response against antigens, but also enhance the production of virus-specific antibodies as well as neutralizing antibodies and thus positively modulate an anti-dengue immune response in a subject. While the exact mechanism of action is not completely understood, the immune enhancement observed may be similar to that produced by an adjuvant.

Thus, it is contemplated herein that in various aspects and embodiments, the present invention relates to immune enhancing compositions comprising NS3 helicase polypeptides and/or fragments thereof and methods of enhancing an anti-dengue immune response in a subject against a specific dengue antigen by co-administering the immune enhancing composition with the specific dengue antigen. The method may comprise co-administering a specific dengue antigen with purified and/or recombinant NS3 helicase polypeptide together, or separately. It is contemplated that the methods may comprise the co-administration of NS3 helicase protein with any dengue antigen. It is contemplated herein that in a particular embodiment, the NS3 helicase can be co-administered with a dengue PIV. In addition to the foregoing, it is further contemplated herein that the NS3 helicase and/or fragments thereof may be administered to a subject in the form of a DNA vaccine.

In particular, the invention further relates to methods of increasing the titer of virus-specific IgG antibodies, and/or increasing the titer of IFN-γ responses in a subject in need thereof comprising administering to the subject an effective amount of the NS3 helicase polypeptide and/or fragments thereof (or nucleic acid encoding said polypeptide and/or fragments) disclosed herein. In a particular embodiment, use of the disclosed NS3 helicase polypeptides and/or fragments thereof (or nucleic acid encoding same) as an immunologic adjuvant of viral vaccines is contemplated herein.

In a particular embodiment, the present invention is directed to a method of preventing, ameliorating or treating disease caused by dengue virus in a subject in need thereof comprising administering to the subject a dengue vaccine formulation in combination with a NS3 helicase polypeptide and/or fragment(s) thereof, wherein said method comprises stimulating humoral as well as cell-mediated immunity to the dengue virus in the subject.

Also contemplated herein are compositions which comprise a dengue vaccine formulation and a NS3 helicase polypeptide and/or fragments thereof. In a particular embodiment, the composition is an immunogenic composition comprising an effective amount of a recombinant NS3 helicase polypeptide and/or fragments thereof, an effective amount of purified dengue virus antigen, a pharmaceutically acceptable excipient, and an effective amount of adjuvant.

In particular embodiments of the above aspects, the fragment comprises T cell epitopes. In a particular embodiment, the fragment contains amino acids 174-560 of the NS3 helicase. In another embodiment, the fragment contains amino acids 200-324 of the NS3 helicase. In a particular embodiment, the NS3 helicase polypeptide is a recombinant protein.

In particular embodiments of the above mentioned aspects the dengue vaccine formulation is directed against one or more dengue viruses of serotypes 1-4. In a particular embodiment, the dengue vaccine formulation comprises one or more antigens selected from the group consisting of a Dengue-1 virus antigen, a Dengue-2 virus antigen, a Dengue-3 virus antigen and a Dengue-4 virus antigen. In a particular embodiment, the dengue vaccine formulation is a dengue purified inactived vaccine. In a particular embodiment, the dengue vaccine formulation is a tetravalent dengue purified inactived vaccine. In another embodiment, the dengue vaccine formulation is a dengue virus-2 purified inactivated vaccine.

In addition to dengue, it is contemplated herein that other flaviviruses may be similarly treated according to the methods of the instant invention, e.g., by combining a flavivirus vaccine in combination with NS3 helicase protein and/or fragments thereof, as disclosed herein. Flavivirus is a genus in the Flaviviridae family of viruses and are familiar to one of skill in the art. Thus, in addition to dengue virus, these viruses include, e.g., the West Nile virus, tick-borne encephalitis virus, yellow fever virus, and Zika virus.

One of skill in the art will appreciate that a vaccine formulation and the NS3 helicase may be produced and administered to a subject according to a variety of conventional methods. Thus, in a particular embodiment, the vaccine formulation and/or the NS3 helicase may be administered in the form of a DNA vaccine. "DNA vaccines" are familiar to one of skill in the art and comprise administering genetic material encoding a particular antigen of interest, e.g., in the form of plasmid DNA comprising nucleic acid encoding the antigen, into a subject. Expression of the genetic material in the subject can then trigger an immune response against the expressed antigen in the subject. Thus, it is understood herein that one or more viral antigens for use in the methods and compositions of the instant invention may be administered to a subject to induce an immune response not only in the form of a purified or a recombinant protein, but also in the form of nucleic acid encoding the antigen, e.g., as a DNA plasmid, for expression in the subject.

One of skill in the art will appreciate that, as used herein, the term "antigen" is a compound, composition, or substance that can stimulate the production of antibodies and/or a T cell response in a subject, including compositions that are injected, absorbed or otherwise introduced into a subject. The term "antigen" includes all related antigenic epitopes. The term "epitope" or "antigenic determinant" refers to a site on an antigen to which B and/or T cells respond. The term "T-cell epitope" refers to an epitope that when bound to an appropriate MHC molecule is specifically bound by a T cell (via a T cell receptor). A "B-cell epitope" is an epitope that is specifically bound by an antibody (or B cell receptor molecule).

As used herein, the terms "dengue vaccine" and "dengue vaccine formulation" may be used interchangeably, and include but are not limited to, existing monovalent and polyvalent dengue vaccines familiar to one of skill in the art.

As used herein, the term "NS3 helicase polypeptide" or the "NS3 helicase polypeptide and/or fragments thereof" may be used interchangeably herein and encompass the entire NS3 helicase polypeptide sequence, as well as one or more fragments thereof, from a dengue virus or other flavivirus. It is understood herein that use of the NS3 helicase polypeptide and fragments thereof referred to herein also encompasses the use of nucleic acid encoding said helicase and fragments.

As one of skill in the art will appreciate, an "immune response" is a response of a cell of the immune system, such as a B cell, T cell, or monocyte, to a stimulus. An immune response can be a B cell response, which results in the production of specific antibodies, such as antigen specific neutralizing antibodies. An immune response can also be a T cell response, such as a CD4+ response or a CD8+ response. In some cases, the response is specific for a particular antigen (that is, an "antigen-specific response"). A "protective immune response" is an immune response that inhibits a detrimental function or activity of a pathogen, reduces infection by a pathogen, or decreases symptoms (including death) that result from infection by the pathogen. A protective immune response can be measured, for example, by the inhibition of viral replication or plaque formation in a plaque reduction assay or ELISA-neutralization assay, or by measuring resistance to pathogen challenge in vivo.

As understood herein, enhancing an immune response in a subject provides a meaningful clinical benefit to the subject. Such benefit may be, e.g., preventing, ameliorating, treating, inhibiting, and/or reducing one of more pathological conditions associated with a viral infection, e.g., dengue infection, or related sequelae, in the subject. Thus, the methods of the present invention can be considered therapeutic methods or preventative or prophylactic methods. In a particular embodiment, it is contemplated herein that the immunogenic compositions of the instant invention may be administered to a subject and thus treat, prevent, and/or ameliorate a disease caused by one or more dengue viruses by inducing both an enhanced humoral response as well as an enhanced cellular immune response in the subject.

As understood herein, the methods and compositions of the instant invention may be employed in order to induce or enhance an immune response in a subject in need thereof and thus treat, prevent and/or ameliorate one or more pathological conditions associated with dengue virus in the subject. As used herein, the terms, "induce", "enhance", "immune enhancing", "enhancement of immunity", "modulator of immune responses to antigen" and like terms encompass any increase in immunity, and any measure of immunity, including enhancement of cellular and/or humoral immunity and/ or by protective efficacy of an antigen, in a subject. In a particular embodiment, it is contemplated herein that the administration of an NS3 helicase polypeptide and/or fragments thereof in combination with a dengue vaccine can enhance the immune response stimulated by the dengue vaccine formulation alone. In another embodiment, it is contemplated herein that both humoral and cellular immune responses are enhanced in a subject by the methods and compositions of the instant invention.

As understood herein, a "subject", a "subject in need thereof" and like terms are interchangeable and includes humans as well as non-humans who would benefit from the methods and compositions of the instant invention. In a particular embodiment, the subject is a human patient. The term "patient" refers to any human being that is to receive a viral vaccine, e.g., a dengue vaccine, in combination with an NS3 helicase compositions described herein. The patient may already be infected with the virus or may be at risk of infection.

As used herein, an "immunogenic composition" and like terms encompass compositions that may be administered to a subject in need thereof (e.g., human or animal) in order to enhance an immune response against a flavivirus. As such, an immunogenic composition comprises one or more antigens (for example, whole purified dengue virus or antigenic subunits, e.g., polypeptides, thereof) or antigenic epitopes. In a particular embodiment, such immunogenic compositions comprise dengue vaccine formulations. It is contemplated herein that an immunogenic composition of the instant invention further comprises an NS3 helicase domain polypeptide and/or fragments thereof. Such compositions may further comprise an effective amount of one or more additional agents, e.g., one or more pharmaceutical excipients, carriers, and/or adjuvants.

It is contemplated herein that in a particular embodiment, an immunogenic composition of the instant invention may comprise an NS3 helicase polypeptide and/or fragments thereof and may be administered to a subject alone or in combination with an immunogenic composition which comprises one or more purified inactivated flavivirus antigens. For example, an immunogenic composition may be a dengue vaccine formulation comprising a single strain of dengue virus (i.e., a monovalent composition), or may comprise more than one strain of dengue virus (i.e., a multivalent composition). In one embodiment, a vaccine formulation of the instant invention is a multivalent formulation. In a particular embodiment, the vaccine formulation is a polyvalent formulation against two or more dengue viruses, including but not limited to, any two or more of dengue serotypes 1-4. In a particular embodiment, the immunogenic composition is a tetravalent dengue vaccine formulation comprising strains selected from each of the four serotypes of dengue virus.

In a particular embodiment, the immunogenic compositions of the instant invention are pharmaceutical compositions comprising a flavivirus vaccine formulation, e.g., a dengue vaccine formulation, and further comprising an NS3 helicase polypeptide and/or fragments thereof. In various embodiments, such pharmaceutical compositions may further comprise other active agents and/or one or more pharmaceutically acceptable excipients which are contemplated for administration to a subject as provided herein.

In another embodiment, the immunogenic compositions of the instant invention may comprise DNA vaccines that comprise expression plasmids comprising one or more nucleic acid sequences encoding an NS3 helicase polypeptide, and/or encoding fragments thereof. In a particular embodiment, a DNA vaccine of the present invention may comprise the DNA sequence provided herein as SEQ ID NO. 5 encoding an NS3 helicase polypeptide (SEQ ID NO. 6) and/or immunogenic fragments thereof (see FIG. 6 and FIG. 7).

As contemplated herein, immunogenic compositions are administered to a subject to elicit an immune response that protects the subject against symptoms or conditions induced by a pathogen. In some cases, symptoms or disease caused by a pathogen are prevented (or treated, e.g., reduced or ameliorated) by inhibiting replication of the pathogen following exposure of the subject to the pathogen. In a particular embodiment, the immunogenic compositions disclosed herein are suitable for preventing, ameliorating and/or treating disease caused by infection with flavivirus, e.g., dengue virus.

In the context of this disclosure, the term immunogenic composition will be understood to encompass compositions that are intended for administration to a subject or population of subjects for the purpose of eliciting a protective or palliative immune response against a flavivirus, e.g., dengue (that is, vaccine compositions or vaccines). Thus, one of skill in the art will appreciate that the concept of "preventing and/or ameliorating" one or more pathological conditions associated with a flavivirus encompasses, e.g., averting or hindering the onset or development of a pathological condition associated with a flavivirus infection, e.g., a dengue infection, as well as treating, curing, retarding, and/or reducing the severity of one or more pathological conditions associated with flavivirus infection, including preventing dengue fever, DHF and/or DSS, and/or reducing the severity or duration of disease associated with dengue.

As discussed above, it is contemplated herein that the dengue vaccine formulations for administration to a subject in combination with NS3 helicase polypeptide as disclosed herein may be based on one or more strains of dengue virus. For example, a dengue vaccine may be based on one or more virus strains selected for each serotype, such as DEN-1, DEN-2, DEN-3, and/or DEN-4, and may be designed by a clinician in response to the needs of the subject. Such a virus can be naturally occurring or synthetic. Examples of dengue virus strains are described in U.S. Pat. No. 6,254,873 which is incorporated by reference herein. Additional suitable strains are disclosed, e.g., in U.S. Pat. No. 7,226,602, which is also incorporated by reference herein. Additional strains can be found, for example, in various online viral genome databases which are familiar to and easily accessible by one of skill in the art.

One of skill in the art may formulate a flavivirus vaccine for use in the methods and compositions of the instant invention using conventional methods. For example, the dengue vaccines for use in the methods of the instant invention include, but are not limited to, live vaccines such as live attenuated virus vaccines, live recombinant vaccines, and live chimeric virus vaccines. Inactivated vaccines may also be used in the methods of the instant invention. These include, but are not limited to, purified inactivated dengue virus vaccines ("PIV vaccines"). Such vaccines are familiar to one of skill in the art and typically comprise a dengue virus antigen which is a whole killed or inactivated virus. The term "inactivated" in the context of a dengue virus vaccine means that the antigenic component (e.g., virus) is incapable of replication in vivo or in vitro. The dengue vaccines for use in the instant invention also include but are not limited to DNA and subunit vaccines (see e.g., Wan et al., Journal of Biomedical Science, 20:37-45 (2013)).

Dengue PIVs for use in the methods of the instant invention include, e.g., inactivated DENV-1, DENV-2, DENV-3 and DENV-4 vaccines. In a particular embodiment, a DENV PIV for use in the instant invention is a DENV-2 PIV. Such vaccines are familiar to and may be formulated using conventional methods by one of skill in the art. In one embodiment, the dengue vaccine formulation may comprise, e.g., the DENV capsid (C), premembrane (prM), and envelope (E) antigens, along with smaller amounts of non-structural protein 1 (NS1) (Putnak, et al., J. Inf. Dis., 174: 1176-84 (1996)). Inactivated dengue virus vaccines are also described, e.g., in U.S. Pat. No. 6,254,873; DNA vaccines are described in U.S. Pat. No. 6,455,509 B1; recombinant vaccines are described in WO2014204892 A1; chimeric virus vaccines are described in WO2014016362 A1, the entire contents of all of which are incorporated by reference herein.

The NS3 helicase polypeptides and/or other antigens for use in the compositions and methods of the instant invention may be produced by recombinant means according to conventional methods familiar to one of skill in the art. These include a variety of expression systems, including, e.g., cell cultures employing E. coli, yeast, and baculovirus. One of skill in the art will be able to select an appropriate expression system, i.e., a system that can produce recombinant proteins with the appropriate (e.g., native-like) structure necessary to generate an immune response in vivo, and generate recombinant proteins for use in the methods and compositions of the instant invention without undue experimentation.

As used herein, an "effective amount", "therapeutically effective amount", "immunologically effective amount" and like terms refer to, e.g., the amount of a vaccine formulation and/or amount of an NS3 helicase polypeptide, alone or in combination in a composition (as the case may be), that produces a desired enhancement in immune response in a subject. In a particular embodiment, the amount produces an enhancement in both cellular and humoral immune responses in the subject.

"Pharmaceutical compositions" are familiar to one of skill in the art. As understood herein, in a particular embodiment, a pharmaceutical composition of the instant invention comprises a flaviviral vaccine formulation, e.g., a dengue vaccine formulation, in combination with an immunogenically effective amount of an NS3 helicase polypeptide and/or fragments thereof (and/or a DNA vaccine comprising a DNA construct (e.g., plasmid) encoding an NS3 helicase polypeptide or fragments thereof) in combination with one or more pharmaceutically acceptable excipients, carriers, or diluents.

The term "pharmaceutically acceptable" is understood herein to refer to a non-toxic material that is compatible with a biological system such as a cell, cell culture, tissue, or organism. Examples of pharmaceutically acceptable excipients, carriers and diluents are familiar to one of skill in the art and can be found, e.g., in Remington's Pharmaceutical Sciences, Mack Publishing Company, Easton, Pa. 5$^{th}$ Edition (1975). For example, pharmaceutically acceptable excipients include, but are not limited to, wetting or emulsifying agents, pH buffering substances, binders, stabilizers, preservatives, bulking agents, adsorbents, disinfectants, detergents, sugar alcohols, gelling or viscosity enhancing additives, flavoring agents, and colors. Pharmaceutically acceptable carriers include macromolecules such as proteins, polysaccharides, polylactic acids, polyglycolic acids, polymeric amino acids, amino acid copolymers, trehalose, lipid aggregates (such as oil droplets or liposomes), and inactive virus particles. Pharmaceutically acceptable diluents include, but are not limited to, water, saline, and glycerol.

As understood by one of skill in the art, the type and amount of pharmaceutically acceptable components included in the pharmaceutical compositions of the instant invention may vary, e.g., depending upon the desired route of administration and desired physical state, solubility, stability, and rate of in vivo release of the composition. For example, for administration by intravenous, cutaneous, subcutaneous, or other injection, a vaccine formulation is typically in the form of a pyrogen-free, parenterally acceptable aqueous solution of suitable pH and stability, and may contain an isotonic vehicle as well as pharmaceutical acceptable stabilizers, preservatives, buffers, antioxidants, or other additives familiar to one of skill in the art.

As contemplated herein, in addition to an immunologically effective amount of active immunogenic substances, the formulations and compositions of the instant invention may further comprise one or more non-immunogenic components, e.g., one or more pharmaceutically acceptable excipients, carriers, diluents, stabilizers, preservatives, buffers, and disinfectants as discussed above. To this end, for example, one of skill in the art will appreciate that the development of a robust and stable vaccine formulation will ideally employ various excipients and formulation parameters that will provide stability to the antigen and thus prevent aggregation, loss of protein structure, and/or chemical degradation such as oxidation and deamidation. One of skill in the art using routine experimentation and conventional methods can determine the particular pH, buffers, and stabilizers that are well suited for the development of robust and stable vaccine formulations of the instant invention. See, e.g., Morefield, G. (2011) The APPS Journal, 13: 191-200; Remington's Pharmaceutical Sciences, Mack Publishing Co., Easton, Pa., 5th Edition (1975).

In addition, the formulations and compositions of the instant invention may comprise pharmaceutically acceptable substances which can produce and/or further enhance an immune response in a subject. These substances include, but are not limited to, adjuvants familiar to one of skill in the art. As understood by one of skill in the art, an adjuvant is a substance that aids a subject's immune response to an antigen. An adjuvant can be used to increase the immunogenic efficacy of a vaccine, and may also have the ability to increase the stability of a vaccine formulation, i.e., adjuvants are agents that enhance the production of an antigen-specific immune response as compared to administration of the antigen in the absence of the agent. Thus, faster and longer lasting immune responses may be possible in vivo through the addition of an adjuvant to a vaccine formulation. Thus, as understood herein, an "effective amount" of an adjuvant is that amount which is capable of producing an enhanced immune response as described above.

Adjuvants suitable for use with the compositions and vaccines of the instant invention are familiar to one of skill in the art and are available from a variety of commercial vendors. These include, for example, glycolipids; chemokines; compounds that induce the production of cytokines and chemokines; interferons; inert carriers, such as alum, bentonite, latex, and acrylic particles; pluronic block polymers; depot formers; surface active materials, such as saponin, lysolecithin, retinal, liposomes, and pluronic polymer formulations; macrophage stimulators, such as bacterial lipopolysaccharide; alternate pathway complement activators, such as insulin, zymosan, endotoxin, and levamisole; nonionic surfactants; poly(oxyethylene)-poly(oxypropylene) tri-block copolymers; trehalose dimycolate (TDM); cell wall skeleton (CWS); complete Freund's adjuvant; incomplete Freund's adjuvant; macrophage colony stimulating factor (M-CSF); tumor necrosis factor (TNF); 3-O-deacylated MPL; CpG oligonucleotides; polyoxyethylene ethers, polyoxyethylene esters, aluminum, Poly[di(carboxylatophenoxy)phosphazene] (PCPP), monophosphoryl lipid A, QS-21, cholera toxin and formyl methionyl peptide.

In one embodiment, the adjuvant may be selected from the group consisting of antigen delivery systems (e.g. aluminum compounds or liposomes), immunopotentiators (e.g. toll-like receptor ligands), or a combination thereof (e.g., AS01 or ASO4.) These substances are familiar to one of skill in the art. In a particular embodiment, an adjuvant for use in the compositions and methods of the instant invention is selected from the group consisting of toll-like receptor ligands, aluminum phosphate, aluminum hydroxide, monophosphoryl lipid A, liposomes, and derivatives and combinations thereof. See, e.g., Alving, C. et al., 2012, Expert Rev Vaccines 11, 733-44; Alving, C. et al. (2012) Curr Opin Immunol 24, 310-5; Alving C. and Rao, M, (2008) Vaccine 26, 3036-3045; U.S. Pat. No. 6,090,406; U.S. Pat. No. 5,916,588.

It is understood herein that the compositions and vaccines disclosed herein may be administered to a subject alone or in combination with other vaccines, and/or in combination with one or more other active pharmaceutical ingredients including, e.g., other active therapeutic or immunoregulatory agents which can enhance a subject's immune response to a dengue virus, or other virus from the family flaviviridae. Such additional vaccines and active agents may be administered to a subject in any manner, e.g., before, after, or concurrently with one or more immunogenic compositions comprising dengue vaccines and NS3 helicase polypeptides, and/or nucleic acid encoding NS3 helicase polypeptides.

One of skill in the art will appreciate that the methods of the instant invention encompass administration of the immunogenic compositions and flavivirus vaccine formulations disclosed herein to generate immunity in a subject if later challenged by infection with a flavivirus. It is further understood herein, however, that the compositions, vaccine formulations, and methods of the present invention do not necessarily provide total immunity to flavivirus (e.g., dengue virus) and/or totally cure or eliminate all disease symptoms.

Suitable effective amounts of the immunogenic compositions of the instant invention can be readily determined by one of skill in the art and will depend upon, e.g., the age, weight, species (if non-human) and medical condition of the subject to be treated. For example, initial information may be gleaned in laboratory experiments, and an effective amount for humans subsequently determined through conventional dosing trials and routine experimentation; e.g., studies indicate that 25 mg per kg of NS3 helicase protein can be given to monkeys without toxicity. For example, as contemplated herein, an effective amount of an NS3 helicase polypeptide to be used in an immunogenic composition against flavivirus, e.g., a dengue infection, may be from between about 1 µg or less to about 100 µg or more per kg body weight. As a general guide, a suitable amount of a recombinant and/or purified NS3 polypeptide or one or more fragments thereof can be an amount between from about 0.1 µg to about 25 mg per dosage amount, with or without an adjuvant. Moreover, immunization comprising administering one or more boosting doses may be performed using between from about 0.1 µg to about 25 mg per dose, with or without adjuvant.

One of skill in the art will appreciate that DNA vaccines can comprise an optimized gene sequence of interest cloned into a bacterial plasmid. Typically, the amount of antigen produced in vivo after DNA inoculation is in the picogram to nanogram range. Since small amounts of protein are synthesized, an effective amount for humans may be determined through experimentation and dosing trials without undue experimentation. Thus, typically, nucleic acid vaccines may be administered between 1 mg and 5 mg per dose.

It is contemplated herein that the immunogenic compositions of the instant invention may be administered to a subject by a variety of routes according to conventional methods, including but not limited to parenteral (e.g., by intracistemal injection and infusion techniques), intradermal, transmembranal, transdermal (including topical), intramuscular, intraperitoneal, intravenous, intra-arterial, intralesional, subcutaneous, oral, and intranasal (e.g., inhalation) routes of administration. Administration can also be by continuous infusion or bolus injection.

In addition, the immunogenic compositions of the instant invention can be administered in a variety of dosage forms. These include, e.g., liquid preparations and suspensions, including preparations for parenteral, subcutaneous, intradermal, intramuscular, intraperitoneal or intravenous administration (e.g., injectable administration), such as sterile isotonic aqueous solutions, suspensions, emulsions or viscous compositions that may be buffered to a selected pH. In a particular embodiment, it is contemplated herein that the immunogenic compositions of the instant invention are administered to a subject as an injectable, including but not limited to injectable compositions for delivery by intramuscular, intravenous, subcutaneous, or transdermal injection.

In another particular embodiment, compositions of the instant invention may be administered orally. Oral formulations for administration according to the methods of the present invention may include a variety of dosage forms, e.g., solutions, powders, suspensions, tablets, pills, capsules, caplets, sustained release formulations, or preparations which are time-released or which have a liquid filling, e.g., gelatin covered liquid, whereby the gelatin is dissolved in the stomach for delivery to the gut. Such formulations may include a variety of pharmaceutically acceptable excipients described herein, including but not limited to mannitol, lactose, starch, magnesium stearate, sodium saccharine, cellulose, and magnesium carbonate.

In a particular embodiment, it is contemplated herein that a composition for oral administration may be a liquid formulation. Such formulations may comprise a pharmaceutically acceptable thickening agent which can create a composition with enhanced viscosity which facilitates mucosal delivery of the immunogen, e.g., by providing extended contact with the lining of the stomach. Such viscous compositions may be made by one of skill in the art employing conventional methods and employing pharmaceutical excipients and reagents, e.g., methylcellulose, xanthan gum, carboxymethyl cellulose, hydroxypropyl cellulose, and carbomer.

Other dosage forms suitable for nasal or respiratory (mucosal) administration, e.g., in the form of a squeeze spray dispenser, pump dispenser or aerosol dispenser, are contemplated herein. Dosage forms suitable for rectal or vaginal delivery are also contemplated herein. The immunogenic compositions of the instant invention may also be lyophilized and may be delivered to a subject with or without rehydration using conventional methods.

As discussed above, the viral vaccines and other pharmaceutical compositions disclosed herein may be formulated by one of skill in the art using a variety of pharmaceutical excipients, carriers, diluents, etc. familiar to one of skill in the art using art recognized methods. Such vaccines and compositions may be administered to a subject alone, e.g., as individual dosage forms, or administered in combination in the form of an immunogenic composition comprising a flavivirus (e.g., dengue) vaccine formulation(s) and NS3 helicase polypeptide and/or nucleic acid.

In addition to the foregoing, as understood herein, the methods of the instant invention comprise administering the immunogenic compositions of the instant invention to a subject according to various regimens familiar to one of skill in the art, i.e., in an amount and in a manner and for a time sufficient to provide a clinically meaningful benefit to the subject. Suitable administration regimens for use with the instant invention may be determined by one of skill in the art according to conventional methods. For example, it is contemplated herein that an effective amount of an immunogenic composition of the instant invention may be administered to a subject as a single dose, a series of multiple doses administered over a period of days, or a single dose followed by a boosting dose thereafter, e.g., several years later. A “prime boost” schedule may be employed if deemed desirable. The term “dose” or “dosage” as used herein refers to physically discrete units suitable for administration to a subject, each dosage containing a predetermined quantity of a viral vaccine and/or NS3 helicase polypeptide and/or nucleic acid as active pharmaceutical ingredients calculated to produce a desired response on the immune system of the subject.

A viral vaccine may be administered to a subject in conjunction with a NS3 helicase polypeptide or nucleic acid as contemplated herein prior to exposure to infection, or after infection. The administrative regimen, e.g., the quantity to be administered, the number of treatments, and effective amount per unit dose, etc. will depend on the judgment of the practitioner and are peculiar to each subject. Factors to be considered in this regard include physical and clinical state of the subject, route of administration, intended goal of treatment, as well as the potency, stability, and toxicity of the particular construct or composition. As understood by one of skill in the art, a “boosting dose” may comprise the same dosage amount as the initial dosage, or a different dosage amount. Indeed, when a series of immunizations is administered in order to produce a desired immune response in the subject, one of skill in the art will appreciate that in that case, an “effective amount” may encompass more than one administered dosage amount.

As contemplated herein, the immunogenic compositions of the instant invention, and particularly pharmaceutical compositions and vaccines of the instant invention, are preferably sterile and contain an amount of the viral vaccine formulation and NS3 polypeptide/nucleic acid in a unit of weight or volume suitable for administration to a subject. The volume of the composition administered to a subject (dosage unit) will depend on the method of administration and is discernible by one of skill in the art. For example, in the case of an injectable, the volume administered typically may be between 0.1 and 1.0 ml, e.g., approximately 0.5 ml.

The invention also provides kits comprising one or more flavivirus vaccine formulations, e.g., a dengue vaccine formulation, and one or more compositions comprising an NS3 helicase polypeptide and/or fragments thereof, and/or nucleic acid encoding said NS3 helicase polypeptide and/or fragments, of the instant invention. The kit can optionally also contain one or more other therapeutic or immunoregulatory agents. The kits can contain separate doses of the NS3 compositions and flavivirus vaccine formulations for serial or sequential administration, or compositions comprising the active pharmaceutical ingredients in combination. The kits can contain suitable delivery devices, e.g., syringes, inhalation devices, and the like, along with instructions for administrating the compositions. The kits can optionally contain instructions for storage, reconstitution (if applicable), and administration of any or all therapeutic agents included. The kits can include a plurality of containers reflecting the number of administrations to be given to a subject. If the kit contains a first and second container, then a plurality of these can be present.

Although the invention herein has been described with reference to particular embodiments, it is to be understood that these embodiments, and examples provided herein, are merely illustrative of the principles and applications of the present invention. It is therefore to be understood that numerous modifications can be made to the illustrative embodiments and examples, and that other arrangements can be devised without departing from the spirit and scope of the present invention as defined by the appended claims. All patent applications, patents, literature and references cited herein are hereby incorporated by reference in their entirety.

EXAMPLES

The following materials and methods were used to conduct the studies described in the examples provided below.

Recombinant Construct and Protein Expression

The NS3 protein is 618 amino acids (aa) in length containing serine protease and helicase domains required for DENV replication, and out of at least 30 T-cell epitopes, 14 (47%) are clustered within a 124 aa-long stretch from as 200 to as 324 (see FIG. 1). Alignment of consensus amino acid sequences from all four DENV serotypes demonstrated that this region is more conserved (78%) than NS3 as a whole (68%), leading to the conclusion that NS3-derived peptides could be targets for reactivated, DENV cross-reactive T-cells primed by previous infection.

Construction of Expression Plasmids

Expression plasmids containing a $His_6$ tag at the C terminus were constructed as follows. Viral RNA was isolated from DENV-2 (strain S16803) infected Vero cell supernatant. Primers used for the NS3 protease (NS3Pro) fragment were: forward 5'-CATATGGAAGAACAAACACTGACC ATACTC-3' (SEQ ID NO. 1) and reverse 5'-GCGGCCGCATGGAGGTCCATGATGGTCAGTC-3'(SEQ ID NO. 2) containing Nde I and Not I restriction sites, respectively. These primers generated a 708 bp fragment containing the last 40 as of NS2b as well as amino acids 1-196 of NS3 (protease domain). Primers for the NS3 helicase (NS3Hel) fragment were: forward 5'-CATATGGACAACCCAG-AGATCGAAGATGAC-3' (SEQ ID NO. 3) and reverse 5'-GCGGCCGCGTCTGCG TAGTTGATGCCTTCAGC-3' (SEQ ID NO. 4) and generated a 1158 bp fragment containing as 174 to as 560 of the helicase domain. The RT-PCR reactions were performed using the SuperScript III® Platinum One®-Step RT-PCR kit (Invitrogen, Thermo Fisher Scientific, Waltham, Mass.) and the products were cloned into the TOPO®-TA vector (Invitrogen, Thermo Fisher Scientific, Waltham, Mass.). The positive clones were identified, and the plasmid DNAs were digested with Nde I and Not I. The DENV-2 NS3pro and NS3hel fragments were then subcloned into the expression vector pET-30a (+) (Novagen Inc., Madison, Wis.) at the Nde I and Not I sites upstream of the C-terminal 6×His tag. In this vector the inserts are under the control of the lac promoter, which is inducible with IPTG. The integrity of both constructs was verified by sequencing.

Expression and Purification

For the expression of recombinant proteins, the *E. coli* strain BL21 was transformed with the expression plasmids, and cells were grown at 36° C. in LB medium containing kanamycin (100 μg/ml) and 0.5% w/v glucose for 3 hours. Cultures were kept at 4° C. overnight and diluted 100-fold in LB+ medium with antibiotics. Cells were further incubated at 36° C. until the optical density at 600 nm reached 1.0. Cells were then centrifuged at 6000×g and resuspended in glucose-free LB+ containing 1 mM isopropylthiogalactoside (IPTG) (Sigma-Aldrich, St. Louis, Mo.) and incubated at 30° C. for 4 hours. Cells were harvested by centrifugation and the dry pellets stored at −80° C. until use. The bacterial pellets were analyzed by electrophoresis and Western blot. For the purification, pellets were resuspended in Bugbuster extraction reagent (Novagen Inc, Madison, Wis.) containing 0.1% Benzonase and 0.01% rLysozyme and incubated at RT for 20 minutes with gentle rocking. The cellular suspension was centrifuged at 15000×g for 15 minutes and the supernatant removed. The pellet containing inclusion bodies was resuspended in binding buffer (8 M urea, 0.5 M NaCl, 20 mM Tris-HCl pH 7.9, 5 mM imidazole) and clarified by centrifugation at 15000×g for 15 minutes at 4° C. The supernatant was loaded onto a HisPur Ni-NTA affinity column (Thermo Scientific, Rockford, Ill.). The column was washed with several resin bed volumes of 8 M urea, 0.5 M NaCl, 20 mMTris-HCl pH 7.9, 60 mM imidazole until the absorbance of the flow-through fraction at 280 nm approached baseline. His-tagged proteins were eluted with 8 M urea, 0.5 M NaCl, 20 mMTris-HCl pH 7.9, 1 M imidazole. Peak fractions were pooled and refolded by dialysis in PBS in a stepwise manner containing urea in decreasing amounts (6 M, 4 M, 2 M, 1 M every hour and no urea overnight at 4° C.). The dialyzed preparations were concentrated using centrifugal filters with a 10K membrane cut off (Amicon, Ireland). Purified proteins were analyzed by electrophoresis and Western blot. The presence of bacterial lipopolysaccharide in the purified recombinant protein preparations was determined using a Limulus Amoebocyte Lysate (LAL) colorimetric assay (Genscript, Piscataway, N.J.). The endotoxin values for the NS3Pro and NS3Hel were 1.88 EU/mg and 1.7 EU/mg respectively.

SDS-PAGE and Western Blot

Protein samples were mixed with SDS gel loading buffer (Quality Biologicals, Gaithersburg, Md.) and heated for 10 minutes at 70° C. Samples were loaded onto a 4-12% polyacrylamide gel (NuPAGE BT, Life Technologies, Carlsbad, Calif.) and fractionated according to manufacturer's instructions. Protein bands were visualized by staining with Coomassie brilliant blue R-250 (Sigma-Adrich, St. Louis, Mo.). The protein concentrations were measured using the Bradford assay (Bio-Rad, Hercules, Calif.). For the Western blot, protein samples were transferred from the polyacrylamide gel to a PVDF membrane using the Pierce G2 fast blotter (Thermo Scientific, Rockford, Ill.) for 10 minutes. The membrane was blocked with 5% non-fat dry milk in PBS/0.01% Tween 20 for 1 h at 37° C., washed three times with PBS/0.01% Tween 20, and then incubated with DENV-2 hyperimmune mouse ascitic fluid (HMAF) at 1:100 in blocking buffer for 1 h at 37° C. After washing, the secondary antibody was peroxidase-conjugated goat anti-human IgG (Kirkegaard & Perry, Gaithersburg, Md.) diluted in blocking solution and incubated for 1 h at 37° C. The membrane was washed again and the bands were detected by incubation with 3, 3', 5, 5'-Tetramethylbenzidine (TMB) Liquid Substrate System (Kirkegaard & Perry, Gaithersburg, Md.).

Expression of Recombinant NS3 Proteins

The regions of the NS3 proteins encoded by plasmids are shown diagrammatically in FIG. 1. The NS3Pro encodes for the C-terminal 40 amino acids of NS2B and the first 196 NS3 N-terminal amino acids, which enclose the protease domain. The NS3Hel construct encodes 386 C-terminal amino acids (from residues 174 to 560) accounting for about 87% of the helicase domain (FIG. 7). The hexa-histidine-tagged recombinant proteins were expressed as *E. coli* inclusion bodies, dissolved in 8 M urea and purified by Ni-NTA affinity chromatography. SDS-Page analysis and Coomassie Brilliant Blue staining showed a main band with an estimated molecular weight of ~30 kDa for NS3Pro and a main band of ~40 kDa for NS3Hel. Both bands were identified as DENV-2-NS3 recombinant proteins by Western blot using DENV-2 HMAF (data not shown). Conditions for growth of *E. coli* transformed by the His-tagged expression plasmids and purification by metal affinity are described herein.

Immunization of Mice

Seven groups of 20 female DBA/1 mice (Jackson Laboratory, Bar Harbor, Me.) 6-8 weeks old, were immunized by intramuscular (tibialis anterior muscle) inoculation on days 0, 14 and 28 with DENV-2 PIV (340 ng), DENV-2 PIV+NS3Pro (340 ng PIV+75 μg NS3Pro), DENV-2 PIV+NS3Hel (340 ng PIV+75 μg NS3Hel), DENV-2 NS3Pro (75 μg), and DENV-2 NS3Hel (75 μg) adjuvanted with 0.1% aluminum phosphate (Adju-Phos, Accurate Chemical, Westbury, N.Y.). Similarly, groups of mice received 0.1% Adju-Phos (200 ul) as a negative control, and for a positive control two doses (day 0, 14) of $10^7$ plaque forming units of live DENV-2 virus in PBS (100 ul). On days 0, 8, 22 and 35, five mice in each group were sacrificed, bled and the spleen harvested and passed through a nylon mesh to prepare single cell suspensions. Erythrocytes were lysed by brief exposure to ACK lysing buffer (155 mM $NH_4Cl$, 10 mM $KHCO_3$, 190 mM EDTA). Cells were washed, viable cells counted and stored in $LN_2$ until further use.

Animals in this study was reviewed and approved by the Walter Reed Army Institute of Research/Naval Medical Research Center Institutional Animal Care and Use Committee (IACUC) in compliance with all applicable Federal regulations governing the protection of animals in research. Housing and experimental use of the animals were performed in strict accordance to all applicable Federal regulations governing the protection of animals in research. The animals were housed in static micro-isolator (filter top) cages (Lab Products Inc., Maywood, N.J.) containing Alpha-Dri paper bedding (Sheperd Specialty Papers, Kalamazoo, Mich.), which were changed under a laminar flow hood at least two times per week. Commercial rodent ration (Rodent Lab Chow, #5001C, Ralston-Purina, St. Louis, Mo.) and water from individual water bottles was provided ad lib. No more than 6 adults were housed in a single standard-sized cage. Terminal exsanguination of mice was achieved by axillary bleeds. Mice were lightly anesthetized with Ketamine/Xylazine (Ketamine (100 mg/ml) at a dose of 80 mg/kg mixed with Xylazine (20 mg/ml) at a dose of 20 mg/kg) prior to retro-orbital sinus bleeds and heavily anesthetized with Ketamine (100 mg/ml) at a dose of 240 mg/kg mixed with Xylazine (20 mg/ml) at a dose of 60 mg/kg for the terminal axillary bleeds.

Virus

Cell culture supernatant harvested from Vero cells (ATCC, CCL-81) infected with DENV-2 (strain S16803, obtained from Dr. K. Eckels, Walter Reed Army Institute of Research, Silver Spring, Md.) was used as virus stock to prepare antigen for the enzyme-linked immunosorbent assay (ELISA) and for the plaque reduction neutralization test (PRNT).

Enzyme-Linked Immunosorbent Assay (ELISA)

Virus antigen was prepared by polyethylene glycol (PEG 8000) precipitation of DENV-infected and -uninfected Vero cells. PEG adsorbed virus preparations were centrifuged at 10,000 rpm for 30 minutes and pellets resuspended in TNE. Virions and control antigen were stored at −80° C. until used. The analysis of sera from immunized rhesus macaques for DENV-2 antibodies was carried out as previously described. (Simmons, et al. American Journal of Tropical Medicine and Hygiene, 65:420-426 (2001)). Briefly, microtiter plates were coated with DENV-2 virions in PBS at 4° C. overnight followed by blocking with 5% non-fat dry milk in PBS/0.01% Tween 20 for 1 h at 37° C. Plates were then incubated with the test sera at twofold serial dilutions starting at 1:100 in blocking buffer for 1 h at 37° C. The secondary antibody was peroxidase-conjugated goat anti-human IgG (Kirkegaard & Perry, Gaithersburg, Md.) diluted in blocking solution and incubated for 1 h at 37° C. The 2.2' azinodi(3ethyl benzthiazoline sulfonate (6)) (ABTS) peroxidase substrate system (Kirkegaard & Perry, Gaithersburg, Md.) was used to visualize dengue virus-specific antibody. The net optical density (OD) values were determined by subtracting the absorbance of test serum with negative control antigen from the absorbance of test serum with the DENV-2 antigen. Endpoint dilution titers were determined by the dilution at which the OD value was at ≥0.10.

Interferon-γ ELISPOT

For the detection of IFN-γ secreting T cells an ELISPOT assay was performed on blinded samples. Cryopreserved mouse splenocytes from day 35, inoculated with PIV, PIV-Pro, PIV-Hel, protease and helicase, as well as adjuvant (negative control) and virus (positive control) were thawed, washed, and brought to $2 \times 10^6$ cells/ml in complete medium (RPMI 1640 (w/o 1-Glutamine) (Mediatech, Manassas, Va.), 1% penicillin, (Invitrogen, Frederick, Md.), 1% 1-glutamine, 1% non-essential amino acids (Mediatech, Manassas, Va.), and 10% heat-inactivated fetal bovine serum (Hyclone Laboratories, Logan, Utah). A peptide pool containing overlapping peptides derived from the whole length of NS3 (DENV-2, New Guinea C) (BEI Resources, Manassas, Va.) and prM and 80% of E (DENV-2 16803) (AnaSpec Inc, San Jose, Calif.) was used to stimulate T cells at a final concentration of 1 μg/ml per peptide. Non-stimulated and concanvalin A (Con A 10 μg/ml) stimulated cells were used as negative and positive controls, respectively.

MultiScreen™ MAIPSWU10 96-well plates (EMD Millipore, Billerica, Mass.) were coated with 100 μl/well of 10 μg/ml anti-human IFN-γ in PBS at room temperature for 3 h. The plates were washed with RPMI 1640 and blocked for 1 h. One hundred microliters of the cell suspension ($2 \times 10^6$ cells/ml) plus 100 μl of the peptide pool or media control were added to duplicate wells, and cultures were incubated for ~24 h at 37° C. in a 5% $CO_2$ humidified atmosphere. The cell cultures were decanted, and the plates were washed six times with PBS/polysorbate 20 (i.e., Tween 20) (Sigma Aldrich, St. Louis, Mo.), followed by 2-h incubation at room temperature with 100 ul/well of the biotin-anti-IFN-γ in PBS. The plates were washed six times, and 100 ul of streptavidin-horse radish peroxidase was added to each well for an additional 90 minutes at room temperature. For color development, the plates were washed again six times, and 100 μl/well of substrate (3-amino-9-ethylcarbazole) (Vectors Laboratories, Burlingame, Calif.) was added to each well. When reddish spots emerged, the plates were washed under tap water to end the reaction. The spots were counted using the AID EliSpot Reader (AID Autoimmun Diagnostika, Strassberg, Germany). IFN-γ responses specific to the NS3, M or E peptide pools were scored as the mean number of spots in duplicate cultures after subtracting the mean background values detected in splenocytes incubated with medium only. The data were then normalized and presented as the mean of the antigen-specific spot forming units per $10^6$ cells. The SD of the mean for duplicates was <20%.

T Cell Depletions

For the CD4+ or CD8+ T cell depletion, the protocol provided by Miltenyi Biotec (Auburn, Calif.) was used. Briefly, spleen cells from Day 35 were thawed and stained with either anti-mouse CD4+-FITC or CD8+-FITC (BD Biosciences, Franklin Lakes, N.J.) for 30 minutes on ice. After staining, the cells were washed twice and then stained with anti-FITC-microbeads (Miltenyi Biotec, Auburn, Calif.). The cells attached to the microbeads were then separated on a magnetic column and non-attached cells were eluted. Depletion of T cell subsets was confirmed by flow cytometry. Briefly, eluted cells were co-stained with anti-mouse CD4-PerCp-Cy5.5 (L3T4) (RM4-5) and CD8a-APC (ly-2) (53-6.7) (all from BD Biosciences, Franklin Lakes, N.J.) on ice for 30 minutes. The stained cells were acquired on FACS Canto II with FACSDiva software (BD Biosciences, Franklin Lakes, N.J.) and data was analyzed by comparing the percentages of CD4+ or CD8+ T cells before and after the process of depletion. For the measurement of IFN-γ, the eluted cells were washed three times and plated for the ELISPOT assay.

Plaque Reduction Neutralization Assay

Plaque-reduction neutralization tests (PRNTs) were performed to measure DENV neutralizing antibodies, using a method modified from that originally described (Russell, P. K., A. Nisalak, J. Immunology, 99: 291-6 (1967)). Vero cell monolayers were seeded in six-well plates (Falcon; Becton Dickinson, Lincoln Park, N.J.) and incubated at 37° C. in a $CO_2$ incubator. Sera from immunized rhesus macaques were tested using serial twofold dilutions starting at 1:10 until an endpoint was reached. The serum dilutions were mixed with DENV-2 to obtain approximately 50 plaque forming units (PFU) per 0.2 ml, incubated at 37° C. for 30 min, then inoculated onto duplicate wells overlayed with nutrient agarose (EMEM, 2% FBS, 1% agarose). Plaques were visualized on day 4 by staining with 0.02% neutral red in Hank's balanced salt solution. The number of plaques reported for each serum dilution was the average of the duplicate wells. The percent reduction in plaques was calculated by comparison of the results obtained with control sera from unimmunized rhesus macaques. The neutralization titer was the test serum dilution at which 50% plaque reduction occurred (PRNT so titer) determined by probit analysis.

Statistics

Primary analysis included descriptive statistics of each animal's antibody and cytokine responses (e. g. geometric mean and standard deviation). All titers were log transformed to stabilize variance. The Student's t test was used in the data analysis; however, p-values obtained were considered to represent descriptive measure of strength of evidence rather than formal statistical inference. Statistical significance was defined as P<0.05. For calculation purposes, PRNT titers<20 were given a value of 5.

Example 1: Antibody Responses in Mice

Figure 2:
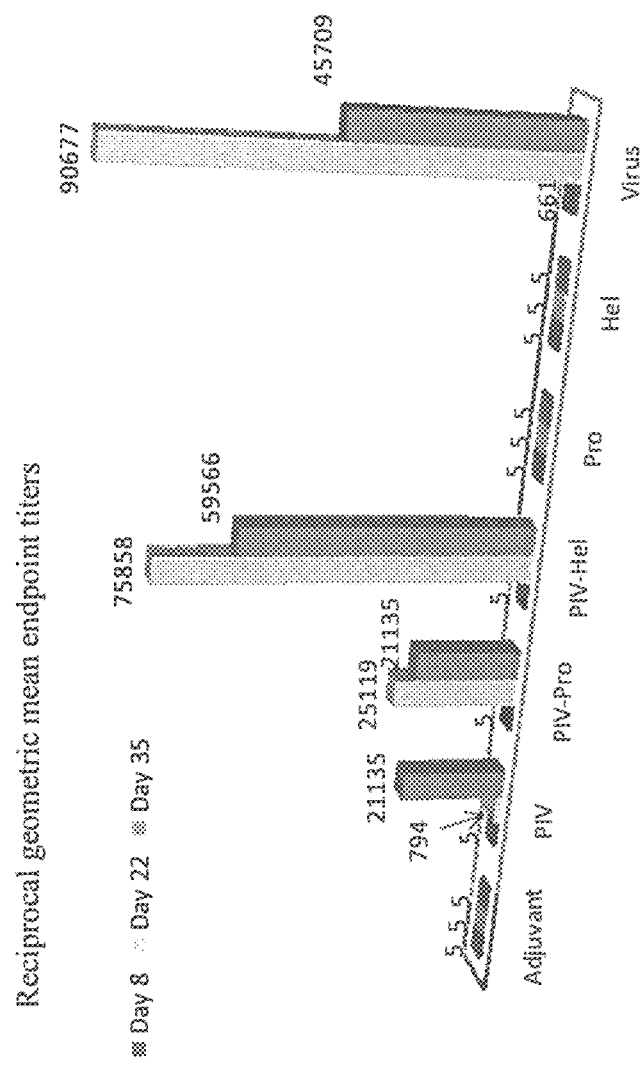

To determine the immunological effect of adding recombinant NS3 proteins to the DENV-2 PIV vaccine, mice were immunized on days 0, 14 and 28 with PIV alone, PIV+NS3Pro, PIV+NS3Hel, protease or helicase alone, DENV-2 (positive control) and adjuvant (negative control). Serotype specific IgG antibody titers of sera from immunized mice were measured by ELISA using DENV-2 antigen. FIG. 2 shows detectable antibody on day 8 was seen only in the virus control group with a geometric mean titer of (GMT) 661. By day 22, the highest reciprocal endpoint dilution titer was seen in the virus control group (GMT=90677), followed by the groups that received PIV-Hel (GMT=75858), PIV-Pro (GMT=25119) and PIV only (GMT=794). On day 35, the GMT for the PIV only group rose to 21135, whereas all other groups indicated a slight decline in antibody titer. No antibody to DENV-2 virus was detected in the adjuvant control group, as well as the groups that received protease or helicase alone. Mice that received either protease or helicase did have IgG antibody to their respective recombinant NS3Pro or NS3Hel in the ELISA (data not shown) indicating the lack of NS3 protein in our DENV-2 antigen preparation.

Figure 3:
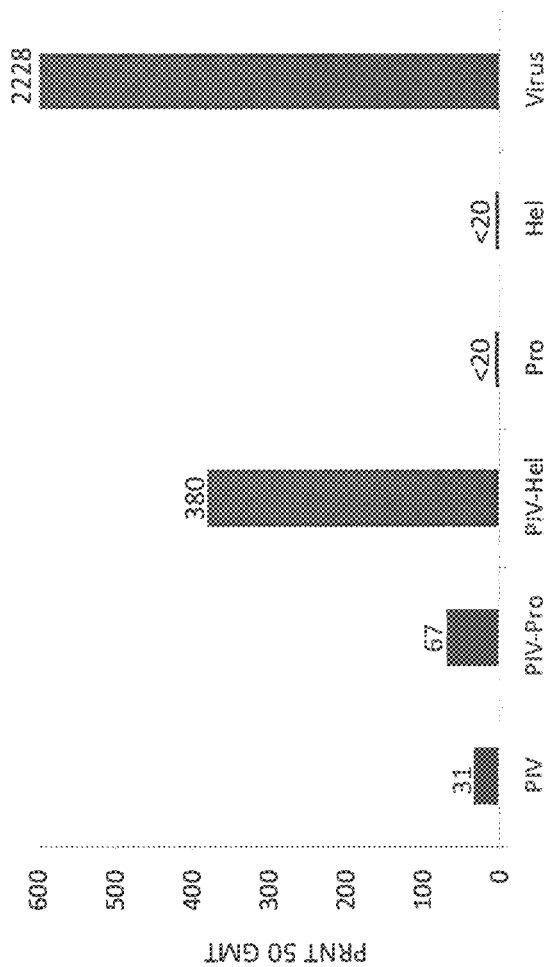

Neutralizing antibodies against DENV-2 were then assayed by 50% plaque reduction neutralization test (PRNT 50) on day 35 (FIG. 3). A similar pattern was observed, with the virus control group showing the highest PRNT 50 GMT of 2228, followed by PIV-Hel with a GMT of 380, PIV-Pro 67 and PIV only group with a GMT of 31. There were no neutralizing antibodies detected on day 22 in any of the groups except one animal in the PIV-Hel group with a titer of 1:36. Similarly, no neutralizing antibody titers were seen in the adjuvant control group as well as the animals receiving protease or helicase preparations. Our results indicate that PIV combined with NS3Hel can generate higher total antibody as well as higher neutralizing antibody titers to DENV-2 in mice than PIV administered alone (p=0.0029).

Non-replicating virus or protein vaccines induce T-dependent responses and require adjuvants to enhance the antibody response. Aluminum salts are frequently used and are included in a majority of currently available vaccines. These adjuvants allow for the slow release of antigen, thereby extending the duration of B cell and T cell activation. The inclusion of additional epitopes on the helicase in our study may have acted as another form of immune modulator by providing additional differentiation and activation signals to monocytes and dendritic cells. This could explain the increased virus-specific IgG antibody (memory) response observed in the PIV-Hel group after the second dose, leading to a significant boost in neutralizing antibody titer after the third immunization.

The addition of helicase to the PIV also resulted in activation of the cellular arm of the immune response as evidenced by the increased IFN-γ response in the PIV-Hel group. CD8+ T cell responses are elicited by vaccines that introduce antigens within the cytosol, and induction of strong CD8+ T cell responses is currently limited to infectious live-attenuated viral vaccines. For non-replicating vaccines the dose of antigen is important for the induction of memory responses. Non-replicating vaccines require sufficient antigen content in addition to adjuvantation for optimal T cell expansion during priming. The addition of a relatively high dose (75 µg) of T cell epitope(s) to the PIV may have increased the magnitude of the initial T cell expansion. For non-replicating vaccines, booster administration is then oriented towards optimization of the primary expansion phase. The persistence of memory B cells and T cells for long-term vaccine efficacy was not evaluated in this study. In our study, the immune-potentiating properties of the recombinant DENV-2 protease (NS2b-aa90 to NS3-aa196) and helicase (NS3-aa174 to aa560) as a source of T cell epitopes in combination with the DENV-2 PIV were evaluated in mice.

The recombinant protease in our study contains all 6 previously identified CD4+ and CD8+ peptide sequences of the protease domain, and the helicase contains 19 (79%) of the 24 previously identified human helicase T-cell epitopes. In addition, the recombinant helicase contains a murine CD8+ (H-2K$^d$) CTL epitope at amino acids 298 to 306 (GYISTRVEM), which was previously shown to be serotype and flavivirus cross-reactive in mice (Spaulding A C, et al. J Virol. 73:398-403 (1999).

Figure 4:
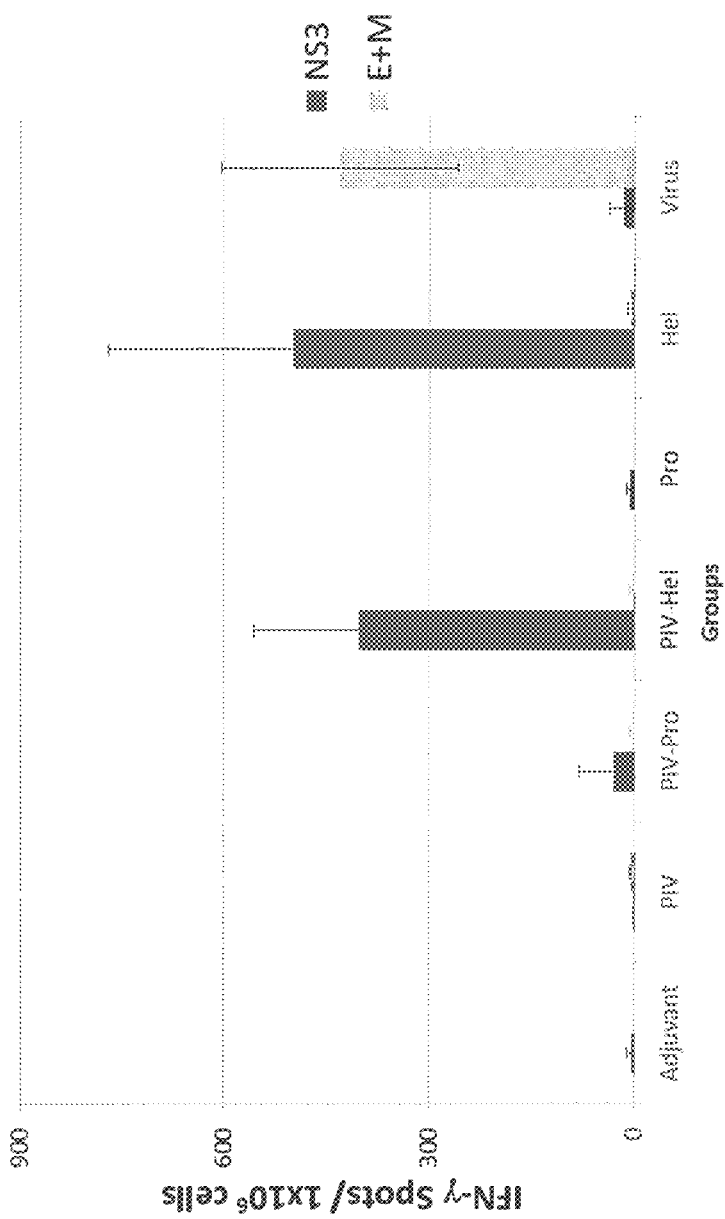
Figure 5:
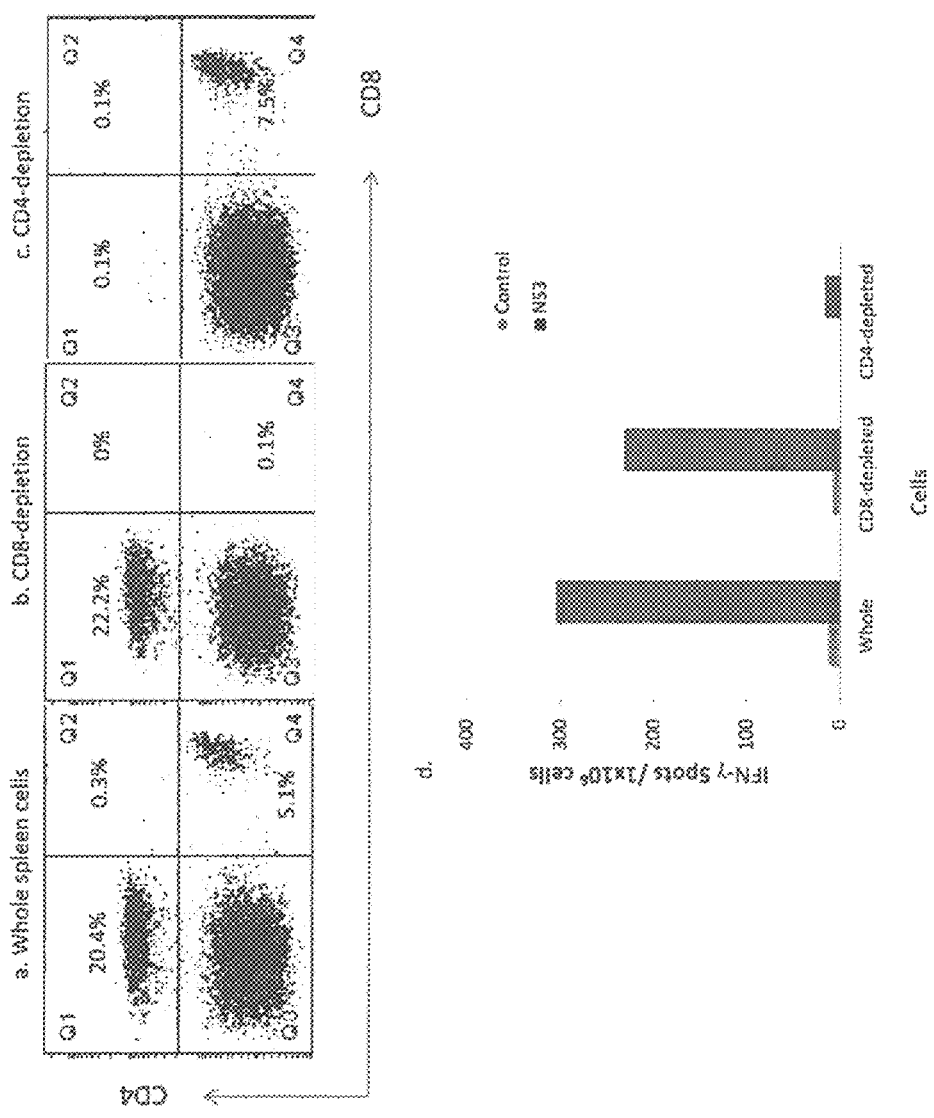

Our results indicate that antibody directed against the DENV-2 protease or helicase were not able to bind or neutralize DENV-2 virus (see FIG. 3 and FIG. 4). Furthermore, Costa et al. has reported that plasmids encoding only the NS3 protease domain did not result in protection, whereas plasmids based on the complete NS3 sequence or the helicase portion resulted in less morbidity and partial protection in mice (Costa S M, PLoS One 6(10):e25685 (2011)). Similarly, the protease domain in our study did not elicit IFN-γ responses and only a minimal increase in neutralizing antibody titer was observed. In contrast, however, in our studies, the helicase domain resulted in a significant increase in IFN-γ responses and neutralizing antibody titers when compared to the PIV alone.

Example 2: Helicase Provides Enhanced Immunity Against the Dengue Antigen

In these studies, cell culture supernatant harvested from Vero cells infected with DENV-2 (S16803) was used as virus stock to prepare antigen for the enzyme-linked immunosorbent assay (ELISA) and for the plaque reduction neutralization test (PRNT).

It was found that NS3 helicase, but not NS3 protease, provides enhanced immunity against antigen, including anti-dengue immunogenic compositions. The enhanced immunity is probably due to T cell-dependent B-cell help. As such, NS3 helicase can be included in immunogenic or vaccine formulations. For example, an immune enhancing composition may comprise the NS3 helicase or fragments of the NS3 helicase such as a helicase polypeptide comprising amino acids 174 to 560 or the T-cell epitope rich region comprising amino acids 200 to 324 of the NS3 helicase region.

Example 3: Production of IFN-γ Induced by NS3 Helicase

An IFN-γ ELISPOT was employed in order to investigate the T-cell response induced by the addition of recombinant NS3 proteins to the PIV vaccine (see FIG. 4). The results surprisingly indicate that only the helicase portion of the non-structural protein NS3 provides improved antibody and cell-mediated immune response.

In these studies, mouse spleen cells were stimulated with overlapping peptides of NS3 and E protein. The highest levels of IFN-γ secreting T cells were detected in the groups that received helicase and the PIV-helicase combination ($p=0.002$), whereas very few (PIV-Pro) or no spots were seen in mice that received adjuvant, PIV or protease alone. The group that received the virus control showed a low level of IFN-γ secretion when stimulated with the NS3 peptide pool but indicated a strong response with the E and M stimulating peptides. As a positive control to confirm cell viability Con A was used as a stimulating antigen (data not shown).

Example 4: CD4+ T Cell Secretion of IFN-γ

To determine if CD4+ or CD8+ T cells are responsible for the IFN-γ secretion, we depleted CD4+ T cells or CD8+ T cells in splenocytes from PIV-Hel immunized mice and measured IFN-γ levels by ELISPOT. Whole or subset depleted cells stained with anti-CD4 or anti-CD8 monoclonal antibodies are shown in FIGS. 5A, 5B and 5C and the depletion process resulted in >98% of depletion of each subset. Stimulation with overlapping NS3 peptides in the ELISPOT showed a strong IFN-γ response in the CD8+ depleted cells but not in the CD4+ depleted cells. CD4+ T cell depleted cells had low levels of IFN-γ similar to the control (unstimulated cells) (FIG. 5D). These results indicate that the observed IFN-γ secretion following co-immunization with DENV-2 NS3 helicase is due to CD4+ T cells.

CD8+ depletion analysis revealed that the IFN-γ response observed in our study is the result of CD4+ T cells. IFN-γ-producing CD4+ T cells generated by vaccination with *Bacillus* Calmette-Guerin (BCG) were shown to protect against *Mycobacterium tuberculosis* (Vogelzang A, et al. J Infect Dis. 210:1928-37 (2014)). A protective antiviral role of CD4+ T cells were also reported for West Nile virus. In one study, CD4+ T cells were shown to help the antibody response, were important for clearance of virus from the CNS and maintaining (but not priming) the CD8+ T cell response (Sitati E M, Diamond M S. J Virol. 80:12060-9 (2006)). Another study found West Nile virus-specific CD4+ T cells exhibited direct antiviral cytokine secretion (IFN-γ, IL-2) and cytotoxicity sufficient for protection (Brien J D, et al. The Journal of Immunology 181:8568-75 (2008)). DENV-specific CD4+ T cells were shown to be involved in supporting B cell antibody production but also play a direct role in viral clearance through production of IFN-γ and expression of CD107a (Rivino L, et al., J Virol. 2012:JVI.02675-12. The contribution of CD4+ T cells to protect against flavivirus infection is virus-specific and may depend on the experimental system used.

Thus, based on the foregoing data, we conclude herein that the addition of recombinant NS3 helicase domain to a killed DENV vaccine can increase virus-specific antibody and neutralizing antibody titers, as well as elicit cell mediated immune responses. Our results indicate that incorporating recombinant NS3 helicase protein as a component of DENV vaccines, and particularly the DENV-2 PIV, may synergistically generate a more effective immune response.

What is claimed is:

1. An immunogenic composition comprising an effective amount of a dengue virus NS3 helicase polypeptide and/or fragments thereof, wherein the NS3 helicase polypeptide fragments are selected from the group consisting of a fragment comprising amino acids 174-560 of the dengue virus NS3 helicase and a fragment comprising amino acids 200-324 of the dengue virus NS3 helicase; an effective amount of one or more adjuvants; and further comprising a purified whole inactivated dengue virus immunogenic composition; wherein said effective amounts of said dengue virus NS3 helicase and/or said one or more adjuvants are sufficient to produce an enhanced immune response to the purified whole inactivated dengue virus immunogenic composition.

2. The immunogenic composition of claim 1 wherein the purified whole inactivated dengue virus immunogenic composition comprises one or more antigens selected from the group consisting of a Dengue-1 virus antigen, a Dengue-2 virus antigen, a Dengue-3 virus antigen and a Dengue-4 virus antigen.

3. The immunogenic composition of claim 2 wherein the purified whole inactivated dengue virus immunogenic composition comprises a Dengue-1 virus antigen, a Dengue-2 virus antigen, a Dengue-3 virus antigen and a Dengue-4 virus antigen.

4. The immunogenic composition of claim 1 wherein the dengue virus NS3 helicase polypeptide and/or fragments thereof are recombinant proteins expressed in vitro.

5. The immunogenic composition of claim 1 wherein said effective amounts of said dengue virus NS3 helicase and/or said one or more adjuvants are sufficient to produce both an enhanced humoral immune response and a cellular immune response to the purified whole inactivated dengue virus immunogenic composition.

6. The immunogenic composition of claim 2 wherein the antigen is a Dengue-2 virus antigen.

7. A method of enhancing an immune response against dengue virus in a subject in need thereof comprising administering to the subject the immunogenic composition of any one of claims 1, 2, 3, 4, 5, and 6, wherein said method comprises stimulating humoral as well as cell-mediated immunity to the dengue virus in the subject.

8. The method of claim 7 wherein the purified whole inactivated dengue virus immunogenic composition and the NS3 helicase polypeptide and/or fragments thereof are administered separately.

9. The method of claim 7 wherein the purified whole inactivated dengue virus immunogenic composition and the NS3 helicase polypeptide and/or fragments thereof are administered together.

10. The method of claim 9 wherein the purified whole inactivated dengue virus immunogenic composition comprises the NS3 helicase and/or fragments thereof as an additional active pharmaceutical ingredient.

11. The method of claim 7 wherein said method of enhancing an immune response against dengue virus comprises enhancing an immune response against any one or more dengue viruses selected from the group consisting of Dengue-1 virus, Dengue-2 virus, Dengue 3 virus, and Dengue-4 virus.

12. The method of claim 11 wherein said any one or more dengue viruses is Dengue-2 virus.

* * * * *